United States Patent
Cook et al.

[11] Patent Number: 5,962,444
[45] Date of Patent: Oct. 5, 1999

[54] 17β-NITRO-11β-ARYLSTEROIDS AND THEIR DERIVATIVES HAVING AGONIST OR ANTAGONIST HORMONAL PROPERTIES

[75] Inventors: C. Edgar Cook, Staunton, Va.; John A. Kepler, Raleigh, N.C.; Rupa S. Shetty; Gary S. Bartley, both of Durham, N.C.; David Yue-wei Lee, Chapel Hill, N.C.

[73] Assignee: Research Triangle Institute, Research Triangle Park, N.C.

[21] Appl. No.: 09/086,674

[22] Filed: May 29, 1998

[51] Int. Cl.⁶ .......................... A61K 31/56; C07J 41/00
[52] U.S. Cl. .......................... 514/177; 514/182; 552/520
[58] Field of Search .......................... 552/522; 514/177, 514/182

[56] References Cited

U.S. PATENT DOCUMENTS

| | | |
|---|---|---|
| 4,386,085 | 5/1983 | Teutsch et al. . |
| 4,447,424 | 5/1984 | Teutsch et al. . |
| 4,609,651 | 9/1986 | Rohde et al. . |
| 4,774,236 | 9/1988 | Cook et al. . |
| 4,861,763 | 8/1989 | Cook et al. . |
| 4,871,724 | 10/1989 | Groen et al. . |
| 4,874,754 | 10/1989 | Nique et al. . |
| 4,900,725 | 2/1990 | Nioue et al. . |
| 4,954,490 | 9/1990 | Cook et al. . |
| 5,073,548 | 12/1991 | Cook et al. . |

FOREIGN PATENT DOCUMENTS

| | | |
|---|---|---|
| 0 057 115 | 8/1982 | European Pat. Off. . |
| 0 116 974 | 8/1984 | European Pat. Off. . |
| 0 147 361 | 7/1985 | European Pat. Off. . |
| 0 190 759 | 8/1986 | European Pat. Off. . |
| 0 192 598 | 8/1986 | European Pat. Off. . |
| 0 245 170 | 11/1987 | European Pat. Off. . |
| 0 254 670 | 1/1988 | European Pat. Off. . |
| 0 277 089 | 8/1988 | European Pat. Off. . |
| 0 277 676 | 8/1988 | European Pat. Off. . |
| 0 289 073 | 11/1988 | European Pat. Off. . |
| 0 305 242 | 3/1989 | European Pat. Off. . |
| 0 321 010 | 6/1989 | European Pat. Off. . |
| 0 349 481 | 1/1990 | European Pat. Off. . |
| 0 404 238 | 12/1990 | European Pat. Off. . |
| 0 411 733 | 2/1991 | European Pat. Off. . |
| 0 549 041 | 6/1993 | European Pat. Off. . |
| 287 510 | 2/1991 | Germany . |
| 289 539 | 5/1991 | Germany . |
| 290 198 | 5/1991 | Germany . |
| WO 87/05908 | 10/1987 | WIPO . |
| WO 88/01868 | 3/1988 | WIPO . |
| WO 89/12448 | 12/1989 | WIPO . |
| WO 92/11279 | 7/1992 | WIPO . |
| WO 93/17686 | 9/1993 | WIPO . |
| WO 93/21926 | 11/1993 | WIPO . |
| WO 96/30390 | 10/1996 | WIPO . |
| WO 97/41145 | 11/1997 | WIPO . |

OTHER PUBLICATIONS

Chemical Abstract, AN 78501u, EP 299,913, Jan. 18, 1989.
Chemical Abstract, AN 6285s, FR 2,586,021, Feb. 13, 1987.
Chemical Abstract, AN 154227b, EP 308,345, Mar. 22, 1989.
Chemical Abstract, AN 164959b, EP 310,542, Apr. 5, 1989.
Chemical Abstract, AN 132580a, EP 369,881, May 23, 1990.
Chemical Abstract, AN 93429d, DE 3,621,024, Dec. 23, 1987.
Patent Abstract of US 4,477,445, Oct. 16, 1994.
G. Teutsch, et al., Human Reproduction, vol. 9, Supplement 1, pp. 12 to 31, "History and Perspectives of Antiprogestins from the Chemist S Point of View", 1994.
C. E. Cook, et al., Human Reproduction, vol. 9 Supplement 1, pp. 32 to 39, "Effects of D–Ring Substituents on Anti-progestational (Antagonist) and Progestional (Agonist) Activity of 11β–Aryl Steroids", 1994.
M. J. Van Den Heuvel, et al., Recueil des Travaux Chimiques des Pays–Bas., vol. 112, No. 02, pp. 107 to 112, "Synthesis of 6β–Methyl Analogues of Mifepristone, New Selective Antiprogestagens", 1993.

Primary Examiner—Jose' G. Dees
Assistant Examiner—Barbara Badio
Attorney, Agent, or Firm—Oblon, Spivak McClelland, Maier & Neustadt, P.C.

[57] ABSTRACT

The invention is directed to 17β-nitro-11β-arylsteroids of formula I:

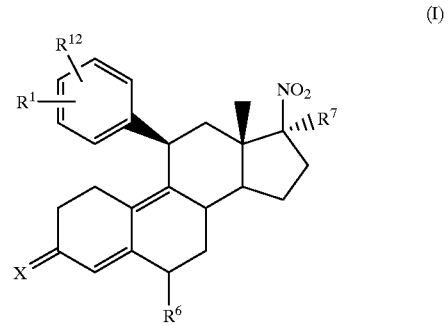

wherein $R^1$, $R^6$, $R^7$, $R^{12}$ and X are as defined by the specification. The compounds exhibit potent antiprogestational activity and are useful in the treatment of fibroids, endometriosis, cervical ripening prior to delivery, hormone replacement therapy and in the control of fertility.

9 Claims, 3 Drawing Sheets a) $CF_3COCF_3$, $Na_2HPO_4$, $H_2O_2$
b) ArMgX, CuCl
c) $H_2NOH$, pyridine
d) N-Bromosuccinimide; $FeSO_4$
e) $NaBH_4$
f) $CH_2=CH-COOEt$, base($\rightarrow R^7 = -CH_2CH_2COOEt$)
   or $HC\equiv C-COOMe$, base($\rightarrow R^7 = -CH=CHCOOMe$)
g) Diisobutylaluminum hydride
h) $CF_3COOH$, $H_2O$, $CH_2Cl_2$ a) NaH, DMSO b) $R^9C\equiv C-Sn(n-Bu)_3$, $Pb(OAc)_4$ (→ $R^9C\equiv C-Pb(OAc)_3$)

c) $CF_3COOH$, $H_2O$, $CH_2Cl_2$

17β-NITRO-11β-ARYLSTEROIDS AND THEIR DERIVATIVES HAVING AGONIST OR ANTAGONIST HORMONAL PROPERTIES

BACKGROUND OF THE INVENTION

1. Field of the Invention

This invention relates to a novel class of steroids which are believed to bind to the progestin receptor and which exhibit potent antiprogestational activity. Such compounds are useful for treatment of fibroids, endometriosis, and certain tumors, in causing cervical ripening prior to delivery, in hormone replacement therapy and in control of fertility and reproduction.

2. Discussion of the Background

Progesterone plays a major role in reproductive health and functioning. Its effects on, for example, the uterus, breast, cervix and hypothalamic-pituitary unit are well established. It also has extra-reproductive activities that are less well studied, such as effects on the brain, the immune system, the vascular endothelial system and on lipid metabolism. Given this wide array of effects, it is apparent that compounds which mimic some of the effects of progesterone (agonists), antagonize these effects (antagonists) or exhibit mixed effects (partial agonists or mixed agonist/antagonist) can be useful in treating a variety of disease states and conditions.

Steroid hormones exert their effects, in-part, by binding to intracellular receptors. Compounds that bind to the appropriate receptors and are antagonists or partial agonists of the estrogenic and androgenic hormones have long been known, but it was not until around 1982 that the discovery of compounds that bind to the progesterone receptor and antagonize the effects of progesterone was announced. Since then, a number of such compounds have been reported in the scientific and patent literature and their effects in vitro, in animals and in humans have been studied. Although compounds such as estrogens and certain enzyme inhibitors can prevent the physiological effects of endogenous progesterone, in this discussion "antiprogestin" is confined to those compounds that bind to the progestin receptor.

Information indicating that antiprogestins would be effective in a number of medical conditions is now available. This information has been summarized in a report from the Institute of Medicine (Donaldson, Molly S.; Dorflinger, L.; Brown, Sarah S.; Benet, Leslie Z., Editors, *Clinical Applications of Mifepristone (RU 486) and Other Antiprogestins*, Committee on Antiprogestins: Assessing the Science, Institute of Medicine, National Academy Press, 1993). In view of the pivotal role that progesterone plays in reproduction, it is not surprising that antiprogestins could play a part in fertility control, including contraception (long-term and emergency or post-coital), menses induction and medical termination of pregnancy, but there are many other potential uses that have been supported by small clinical or preclinical studies. Among these are the following:

1. Labor and delivery—antiprogestins may be used for cervical ripening prior to labor induction such as at term or when labor must be induced due to fetal death. They may also be used to help induce labor in term or post-term pregnancies.

2. Treatment of uterine leiomyomas (fibroids)—these non-malignant tumors may affect up to 20% of women over 30 years old and are one of the most common reasons for surgery in women during their reproductive years. Hysterectomy, the common treatment for persistent symptoms, of course results in sterility.

3. Treatment of endometriosis—this common (5 to 15% incidence, much larger in infertile women) and often painful condition is now treated with drugs such as danazol or gonadotrophin-releasing hormone analogs that have significant side-effects, or must be dealt with surgically.

4. Hormone replacement therapy, where they may be given to interupt or curtail the activity of progestins.

5. Cancers, particularly breast cancers—the presence of progestin receptors in many breast cancers has suggested the use of antiprogestins in treating metatstatic cancer or in prevention of recurrence or initial development of cancer.

6. Other tumors such as meningiomas—these brain membrane tumors, although nonmalignant, result in death of the patient and nonsurgical treatments are lacking.

7. Male contraception—antiprogestins can interfere with sperm viability, although whether this is an antiprogestational effect or not is controversial, as it may relate to the antiglucocorticoid activity of such compounds.

8. Antiestrogenic effects—at least some antiprogestins oppose the action of estrogens in certain tests, but apparently through a mechanism that does not involve classical hormone receptors. This opens a variety of possibilities for their medical use.

9. Antiglucocorticoid effects—this is a common side-effect of antiprogestins, which can be useful in some instances, such as the treatment of Cushing's syndrome, and could play a role in immune disorders, for example. In other instances it is desirable to minimize such effects.

The effects and uses of progesterone agonists have been well documented. In addition, it has been recently shown that certain compounds structurally related to the known antiprogestins have strong agonist activity in certain biological systems (e.g., the classical progestin effects in the estrogen-primed immature rabbit uterus; cf. C. E. Cook et al., Life Sciences, 52, 155–162 (1993)). Such compounds are partial agonists in human cell-derived receptor systems, where they bind to a site distinct from both the progestin and antiprogestin sites (Wagner et al., Proc. Natl. Acad. Sci., 93, 8739–8744 (1996)). Thus the general class of antiprogestins can have subclasses, which may vary in their clinical profiles.

The earliest antiprogestins, in addition to having an 11β-aryl substituent, were substituted with a 17β-hydroxyl group and various 17α-substituents. (See for example, Teutsch, Jean G.; Costerousse, Germain; Philibert, Daniel, and Deraedt, Roger. Novel steroids. U.S. Pat. No. 4,386,085. 1983; Philibert, Daniel; Teutsch, Jean G.; Costerousse, Germain, and Deraedt, Roger. 3-Keto-19-nor-Δ-4,9-steroids. U.S. Pat. No. 4,477,445. 1983; Teutsch, Jean G.; Pantin, Germain; Costerousse, Saint-Maurice; Daniel Philibert; La Varenne Saint Hilaire; Roger Deraedt, inventors. Steroid derivatives. Roussel Uclaf, assignee. U.S. Pat. No. 4,447,424. 1984; Cook, C. Edgar; Tallent, C. Ray; Reel, Jerry R., and Wani, Mansukh C. 17α-(Substituted-methyl)-17β-hydroxy/esterified hydroxy steroids and pharmaceutical compositions containing them. U.S. Pat. No. 4,774,236 (1988) and 4,861,763 (1989)). Then it was discovered that a 17β-acetyl, 17α-acyloxy group in the presence of 11β-aryl could also generate compounds with antiprogestational effects (Cook, C. Edgar; Lee, Y.-W.; Reel, Jerry R.; Wani, Mansukh C., Rector, Douglas. 11β-Substituted Progesterone Analogs. U.S. Pat. Nos. 4,954,490 (1990) and 5,073,548 (1991)), and various permutations of these findings have been made as well. However, introduction of a 16α-ethyl group or a hydrogen substituent at the 17α-position in the 17β-acyl series of compounds is reported to lead to agonist or partial agonist activity (C. E. Cook et al., Life Sciences, 52, 155–162 (1993)).

Generally antiprogestational activity has been associated with the presence of an 11β-aryl substituent on the steroid nucleus, together with a $\Delta^{4,9}$-3-ketone or $\Delta^4$-3-ketone moiety. However, it has been shown that substituents on the D-ring of the steroid can have a marked influence on the biological profile of these compounds (see above). Thus changes in the D-ring of the steroid result in a wide variety of effects on the biological activity.

It can be seen that the 17β-position of current antiprogestins has been characterized by substitution with a carbon or an oxygen atom. No reports have been made of the effect of a nitro or nitro-related substituent such as a spironitrone at the 17β-position in steroids bearing an 11β-aryl substituent. This invention provides a group of novel 17β-nitro steroids, which are characterized by 11β-substitution, particularly 11β-aryl substitution. Very few 17β-nitro steroids and none with 11β-substitution have been reported in either the general chemical literature or in patents. Cf. for example, Patchett, Arthur A.; Metuchen, Glen E.; Arth, Cranford, and Hoffman, Frances G. Alkanoylthio and pyrazolo androstane derivatives. U.S. Pat. No. 3,094,521, 1963. This patent describes a synthesis of 17-nitro steroids and their Michael reaction with methyl acrylate, but no biological activity was reported as associated with the nitro compounds.

In addition, this invention provides a group of novel 17,17-spiro cyclic nitrone steroids. Although a few 17,17-spiro cyclic nitrone steroids are known (cf. Keana, John F. W.; Tamura, Toshinari; McMillen, Debra A., and Jost, Patricia C. Synthesis and characterization of a novel cholesterol nitroxide spin label. Application to the molecular organization of human high-density lipoprotein. J. Am. Chem. Soc. 103: 4904–4912 (1981)), these were used to develop spin labels and not for their biological properties. No such compounds with 11β-aryl substituents have been reported.

In spite of the clinical promise of antiprogestins, as of May 1, 1998, there were no antiprogestin drugs marketed in the United States or many other countries. Only one antiprogestin drug is approved and available for clinical use anywhere in the world and that drug, mifepristone, is mainly used for medical termination of pregnancy. A number of factors are the cause of this situation, but certainly a need exists for new antiprogestational drugs that can be used for the conditions described above. Accordingly there also remains a need for antiprogestin compounds which exhibit higher specificity.

It is therefore the purpose of the present invention to provide novel and potent progestin antagonists (antiprogestins) and mixed or partial progestin agonists, and to provide methods for their medical use in mammals, including humans.

SUMMARY OF THE INVENTION

This invention provides a group of novel 17β-nitro steroids, which are characterized by 11β-substitution, particularly 11β-aryl substitution. In addition, this invention provides a group of novel 17,17-spiro cyclic nitrone steroids. Therefore the present invention is directed to compounds since which have potential for reduction of side effects and, in addition exhibit strong binding to the progestin receptor and have potent progestational or antiprogestational activity.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
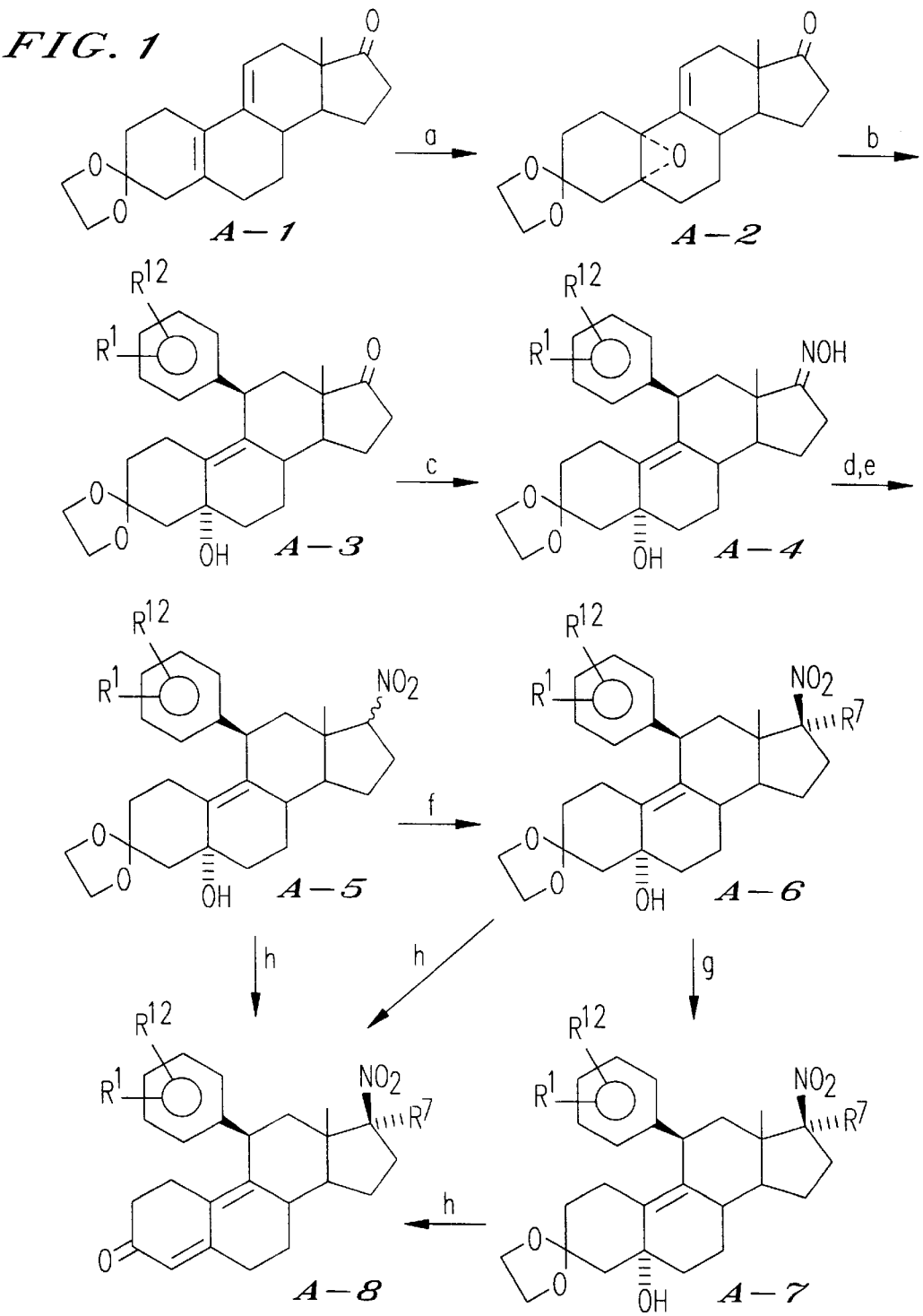
FIG. 1 illustrates the preparation of 17β-nitro substituted compounds.

Steroid compounds according to the present invention may be of the structure I,

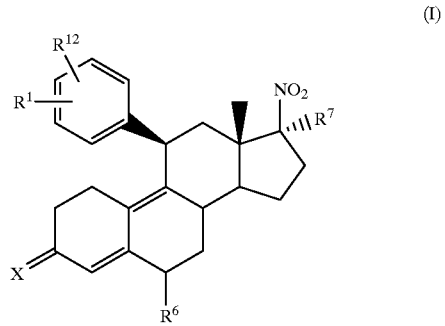

wherein $R^1$ is $(R^2R^3N(O)_r)$—, where r is 0 or 1 and $R^2$ and $R^3$ are each independently H, $C_{1-6}$ alkyl, $C_{3-8}$ cycloalkyl, $C_{2-6}$ alkenyl or $C_{2-6}$ alkynyl, any of which may be optionally substituted; or $R^1$ is

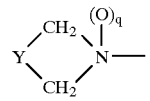

where q is 0 or 1, Y is —$(CH_2)_m$— where m is an integer of 0 to 5, or Y is —$(CH_2)_n$—Z—$(CH_2)_p$—, where n is an integer of 0 to 2, p is an integer of 0 to 2, and Z is a heteroatom (optionally substituted); and where the $CH_2$ groups may be optionally substituted; or $R^1$ is N-imidazolyl-, N-pyrrolyl-, halo-, HO—, $CF_3SO_2O$—, $C_{1-6}$ alkyl O—, $C_{1-6}$ alkyl S—, $C_{1-6}$ alkyl S(O)—, $C_{1-6}$ alkyl $S(O_2)$—, $C_{1-6}$ alkyl CO—, $C_{1-6}$ alkyl CH(OH)—, NC—, HCC—, $C_6H_5CC$—, 2'-furyl, 3'-furyl-, 2'-thiophenyl, 3'-thiophenyl-, 2'-pyridyl, 3'-pyridyl, 4'-pyridyl-, 2'-thiazolyl-, 2'-N-methylimidazolyl-, 5'-pyrimidinyl-, $C_6H_5$—, $H_2C$=CH—, $C_{1-6}$ alkyl or MeC(=$CH_2$)—; and $R^{12}$ is H or halo; or $R^1$ and $R^{12}$ combine to form a ring

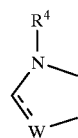

where W is $CH_2$, CH, NH, N, O, or S, and $R^4$ is H or $C_{1-6}$ alkyl; and

X is O or $NOR^5$, where $R^5$ is H or $C_{1-6}$ alkyl, $C_{3-8}$ cycloalkyl, $C_{2-6}$ alkenyl, $C_{2-6}$ alkynyl, $C_{6-12}$ aryl, or heteroaryl, any of which may be optionally substituted; or X is (H, H), (H, OH), (H, OSi($C_{1-6}$ alkyl)$_3$), or (H, OCOR$^5$), where $R^5$ is $C_{1-6}$ alkyl, $C_{3-8}$ cycloalkyl, $C_{2-6}$ alkenyl, $C_{2-6}$ alkynyl, $C_{6-12}$ aryl, aralkyl, aralkenyl, aralkynyl, heteroaralkyl, heteroaralkenyl or heteroaralkynyl, any of which may be optionally substituted; or X is

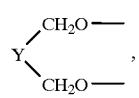

where Y is —$(CH_2)_m$— where m is an integer of 0 to 3, or Y is —$(CH_2)_n$—Z—$(CH_2)_p$—where n is an integer of 0 to 2, p is an integer of 0 to 2 and Z is a heteroatom (optionally substituted) or Z is a carbon atom substituted with one or two $C_{1-6}$ alkyl groups;

$R^6$ is H, $C_{1-6}$ alkyl, or halogen;

$R^7$ is H, $C_{1-6}$ alkyl, $C_{2-6}$ alkenyl, or $C_{2-6}$ alkynyl, $C_{3-8}$ cycloalkyl, $C_{6-12}$ aryl, aralkyl, aralkenyl, aralkynyl, heteroaryl, heteroaralkyl, heteroaralkenyl or heteroaralkynyl, any of which may be optionally substituted, and pharmaceutically acceptable salts thereof.

Steroid compounds according to the present invention may comprise a cyclic nitrone unit, of the structure II,

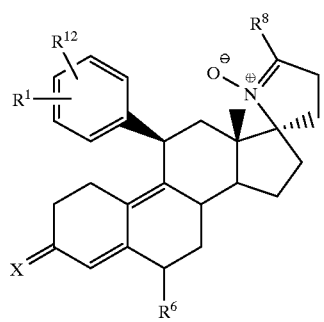

(II)

wherein $R^1$ is ($R^2R^3N(O)_r$)—, where r is 0 or 1 and $R^2$ and $R^3$ are each independently H, Cl$_6$ alkyl, $C_{3-8}$ cycloalkyl, $C_{2-6}$ alkenyl or $C_{2-6}$ alkynyl, any of which may be optionally substituted; or $R^1$ is

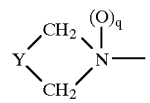

where q is 0 or 1, Y is —$(CH_2)_m$— where m is an integer of 0 to 5, or Y is —$(CH_2)_n$—Z—$(CH_2)_p$— where n is an integer of 0 to 2, p is an integer of 0 to 2, and Z is a heteroatom (optionally substituted) and where the $CH_2$ groups may be optionally substituted; or $R^1$ is N-imidazolyl-, N-pyrrolyl-, halo-, HO—, $CF_3SO_2O$—, $C_{1-6}$ alkyl O—, $C_{1-6}$ alkyl S—, $C_{1-6}$ alkyl S(O)—, $C_{1-6}$ alkyl $S(O_2)$—, $C_{1-6}$ alkyl CO—, $C_{1-6}$ alkyl CH(OH)—, NC—, HCC—, $C_6H_5CC$—, 2'-furyl, 3'-furyl-, 2'-thiophenyl, 3'-thiophenyl-, 2'-pyridyl, 3'-pyridyl, 4'-pyridyl-, 2'-thiazolyl-2'-N-methylimidazolyl-, 5'-pyrimidinyl-, $C_6H_5$—, $H_2C=CH$—, $C_{1-6}$ alkyl or MeC(=$CH_2$)—; and $R^{12}$ is H or halo; or $R^1$ and $R^{12}$ combine to form a ring

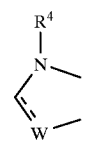

where W is $CH_2$, CH, NH, N, O, or S, and $R^4$ is H or $C_{1-6}$ alkyl; and

X is O or $NOR^5$, where $R^5$ is H or $C_{1-6}$ alkyl, $C_{3-8}$ cycloalkyl, $C_{2-6}$ alkenyl, $C_{2-6}$ alkynyl, $C_{6-12}$ aryl, or heteroaryl, any of which may be optionally substituted; or X is (H, H), (H, OH), (H, OSi($C_{1-6}$ alkyl)$_3$), or (H, OCOR$^5$), where $R^5$ is $C_{1-6}$ alkyl, $C_{3-8}$ cycloalkyl, $C_{2-6}$ alkenyl, $C_{2-6}$ alkynyl, $C_{6-12}$ aryl, aralkyl, aralkenyl, aralkynyl, heteroaryl, heteroaralkyl, heteroaralkenyl or heteroaralkynyl, any of which may be optionally substituted; or X is

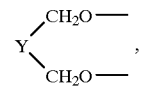

where Y is —$(CH_2)_m$— where m is an integer of 0 to 3, or Y is —$(CH_2)_n$—Z—Z—$(CH_2)_p$— where n is an integer of 0 to 2, p is an integer of 0 to 2 and Z is a heteroatom (optionally substituted) or Z is a carbon atom substituted with one or two $C_{1-6}$ alkyl groups;

$R^6$ is H, $C_{1-6}$ alkyl, or halogen; and $R^8$ is H, $C_{1-6}$ alkyl, $C_{2-6}$ alkenyl, or $C_{2-6}$ alkynyl, $C_{3-8}$ cycloalkyl, $C_{6-12}$ aryl, aralkyl, aralkenyl, aralkynyl, heteroaryl, heteroaralkyl, heteroaralkenyl or heteroaralkynyl, any of which may be optionally substituted, and pharmaceutically acceptable salts thereof.

The above-identified compounds of formula I and II specifically include compounds which are subsitituted on the A ring at the 3-position with two hydrogen atoms. These compounds are believed to undergo oxidation in vivo to the corresponding carbonyl compound.

Within the scope of the present invention, the term heteroatom means oxygen, nitrogen, sulfur, silicon or boron. Halogen means fluorine, chlorine, bromine or iodine and halo means fluoro, chloro, bromo or iodo. Aralkyl, aralkenyl, or aralkynyl means a $C_1$–$C_4$ alkyl, $C_2$–$C_4$ alkenyl or $C_2$–$C_4$ alkynyl group bearing an aryl substituent. Lower alkyl means a $C_1$–$C_4$ alkyl group. Heteroaryl means a unit of 5 to 12 non-hydrogen atoms consisting of one or more cyclic structures that may be fused or linked together, which contain 1 to 5 heteroatoms and which are generally accepted by those skilled in the art as having aromatic electronic character.

Heteroaralkyl, heteroaralkenyl, or heteroaralkynyl means a $C_1$–$C_4$ alkyl, $C_2$–$C_4$ alkenyl or $C_2$–$C_4$ alkynyl group bearing a heteroaryl substituent.

"Optionally substituted" means unsubstituted or substituted with one or more heteroatom(s) and/or halogens and/or alkyl groups of 1 to 4 carbon atoms and/or alkenyl and/or alkynyl groups of 2 to 4 carbon atoms and/or cycloalkyl groups of 3 to 7 carbon atoms and/or aryl groups of 6 to 12 carbon atoms and/or heteroaryl groups, and in which the alkyl, alkenyl, alkynyl, cycloalkyl, aryl or heteroaryl group may be flurther substituted with one or more heteroatoms and/or halogens. Substitution may occur directly on $CH_2$ groups of cyclic amine heterocycles. Where their valency permits, heteroatoms may be substituted either within the carbon chain or by attachment to it by single or double bonds. For example, —$H_2CH_2C(=O)H$, —$CH_2C(=O)CH_3$, —$CH_2CH_2OCH_3$, —$CH_2CH_2CH_2OH$, $CH_3CH_2CH_2O$—, —$CH_2CH_2C(=O)NH_2$, $CH_3CH_2C(=O)NH$—, —$CH_2COOCH_3$, $CH_3CH_2COO$— and $CF_3CC$— all fall within this definition.

In all cases where valency and steric considerations permit, alkyl, alkenyl, alkynyl and cycloalkyl groups may contain additional double or triple bonds and/or branched chains.

The group $R^6$ at $C_6$ as it appears in structures I and II may be in either the α or β position. In a preferred embodiment, the group $R^6$ is located in the α-position.

In another embodiment, the $C_{11}$β-aryl group may be replaced with a pyridine group substituted with groups $R^1$ and $R^{12}$ as previously described.

In a preferred embodiment, the compound of structure I is substituted, where $R^1$-Ph is 4-aminophenyl, 4-(N-methylamino)phenyl, 4-(N,N-dimethylamino)phenyl, 4-(N-piperidino)phenyl, 4-(N-pyrrolidino)phenyl, 4-(N-morpholino)phenyl, 1-methylindol-5-yl or 1-methyl-2,3-dihydroindol-5-yl;

X is O, NOH, or $NOCH_3$;

$R^6$ is H, $CH_3$, F or Cl;

$R^7$ is H, methyl, ethynyl, 1-propynyl, 3-propynyl, 3-hydroxypropyl, 3-hydroxy-1-propenyl (E- or Z-), 3,3,3-trifluropropyn-1-yl, 3-hydroxypropyn-1-yl, $(CH_2)_2COOCH_3$, $(CH_2)_2COOC_2H_5$, $(CH_2)_2COCH_3$, CC—$C_6H_5$, or $CH_2C_6H_{55}$.

In another preferred embodiment, the steroid of structure II is substituted as follows:

$R^1$-Ph is 4-aminophenyl, 4-(N-methylamino)phenyl, 4-(N,N-dimethylamino)phenyl, 4-(N-piperidino) phenyl, 4-(N-pyrrolidino)phenyl, 4-(N-morpholino) phenyl, 1-methylindol-5-yl or 1-methyl-2,3-dihydroindol-5-yl);

X is O, NOH, or $NOCH_3$;

$R^6$ is H, $CH_3$, F or Cl; and $R^8$ is H, $CH_3$ or $CH_2C_6H_5$.

Within the context of the present invention, the individual —$CH_2$— groups which comprise $R^1$ and more specifically, the —$CH_2$— groups of the groups

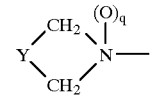

$(CH_2)_m$, $(CH_2)_n$, $(CH_2)_p$ may be substituted as described above.

Specific non-limiting examples include the compounds: 11β-(4-acetylphenyl)-17α-(1-propynyl)- 17β-nitroestra-4,9-dien-3-one; 11β-(4-(N,N-dimethylamino)phenyl)-17α-(1-propynyl)-17β-nitroestra-4,9-dien-3-one; 3',4'-dihydro-11β-(4-(N,N-dimethylamino)phenyl)-5'-methyl-1-oxo-spiro[estra-4,9-dien-17β,2'(2'H)-pyrrole]-3-one; 3',4'-dihydro-11β-(4-(N,N-dimethylamino)phenyl)-1'-oxo-spiro[estra-4,9-dien-17β,2'(2'H)-pyrrole]-3-one; 11β-(4-acetylphenyl)-17α-(E-3-hydroxy-1-propenyl)-17β-nitroestra-4,9-dien-3-one; 11β-(4-acetylphenyl)-17α-(3-hydroxypropyl)-17β-nitroestra-4,9-dien-3-one; 11β-(4-N,N-dimethylamino)phenyl)-17α-(E-3-hydroxy-1-propenyl)-17β-nitroestra-4,9-dien-3-one; 17βnitro-11β-(4-(N-piperidino)phenyl)-17α-propynyl-estra-4,9-dien-3-one; 3',4'-dihydro-11β-(4-(N-piperidino)phenyl)-5'-methyl-1'-oxo-spiro[estra-4,9-diene-17 β, 2'(2'-H)-pyrrole]-3-one; and 11β-(4-(N,N-dimethylamino)phenyl)-17α-(3-hydroxypropyl)-17β-nitroestra-4,9-dien-3-one.

Those compounds of the present invention which bear an amino group on the $C_{11}$ phenyl group accordingly may also comprise a salt formned with the amine. Suitable pharmaceutically acceptable salts are known to those of ordinary skill in the art and comprise carboxylates, sulfates, phosphates and halides.

Steroids having progestational, antiprogestational and/or antiglucocorticoid activity have use in the control of fertility in humans and non-human mammals such as primates, domestic pets and farm animals, and in the treatment of medical conditions in animals or humans in which these activities are beneficial. Thus they may be useful in the treatment of conditions such as fibroids, Cushing's syndrome, glaucoma, endometriosis, cervical ripening prior to delivery, hormone replacement therapy, premenstrual syndrome and cancer in addition to their use in the control of fertility and reproduction.

The compounds of the present invention may be administered by a variety of methods. Thus, those products of the invention that are active by the oral route may be administered in solutions, suspensions, emulsions, tablets, including sublingual and intrabuccal tablets, soft gelatin capsules, including solutions used in soft gelatin capsules, aqueous or oil suspensions, emulsions, pills, lozenges, troches, tablets, syrups or elixirs and the like. Products of the invention active on parenteral administration may be administered by depot injection, implants including Silastic™ and biodegradable implants, intramuscular and intravenous injections.

Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame or saccharin. Ophthalmic formulations, as is known in the art, will be adjusted for osmotic pressure.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the invention suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present.

The pharmaceutical composition of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol. Among the acceptable vehicles and solvents that may be employed are water and Ringer's solution, an isotonic sodium chloride. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Sterilization may be performed by conventional methods known to those of ordinary skill in the art such as by aseptic filtration, irradiation or terminal sterilization (e.g. autoclaving).

Aqueous formulations (i.e oil-in-water emulsions, syrups, elixers and injectable preparations) may be formulated to achieve the pH of optimum stability. The determination of the optimum pH may be performed by conventional methods known to those of ordinary skill in the art. Suitable buffers may also be used to maintain the pH of the formulation.

The compounds of this invention may also be administered in the form of suppositories for rectal administration of the drug. These compositions can be prepared by mixing the drug with a suitable nonirritating excipient which is solid at ordinary temperatures but liquid at the rectal temperatures and will therefore melt in the rectum to release the drug. Non-limiting examples of such materials are cocoa butter and polyethylene glycols.

They may also be administered by intranasal, intraocular, intravaginal, and intrarectal routes including suppositories, insufflation, powders and aerosol formulations.

Products of the invention which are preferably administered by the topical route may be administered as applicator sticks, solutions, suspensions, emulsions, gels, creams, ointments, pastes, jellies, paints, powders, and aerosols.

Products having anti-glucocorticoid activity are of particular value in pathological conditions characterized by excess endogenous glucocorticoid such as Cushing's syndrome, hirsutism and in particular when associated with the adrenogenital syndrome, ocular conditions associated with glucocorticoid excess such as glaucoma, stress symptoms associated with excess glucocorticoid secretion and the like.

Products having progestational activity are of particular value as progestational agents, ovulation inhibitors, menses regulators, contraceptive agents, agents for synchronization of fertile periods in cattle, endometriosis, and the like. When used for contraceptive purposes, they may conveniently be admixed with estrogenic agents, such as for example as ethynylestradiol or estradiol esters.

Products having anti-progestational activity are characterized by antagonizing the effects of progesterone. As such, they are of particular value in control of hormonal irregularities in the menstrual cycle and for synchronization of fertile periods in cattle.

The compounds of the invention may be used for control of fertility during the whole of the reproductive cycle. They are of particular value as postcoital contraceptives, for rendering the uterus inimical to implantation, and as "once a month" contraceptive agents. They may be used in conjunction with prostaglandins, oxytocics, estrogens and the like.

A further important utility for the products of the invention lies in their ability to slow down growth of hormone-dependent cancers. Such cancers include kidney, breast, endometrial, ovarian cancers, and prostate cancer which are characterized by possessing progesterone receptors and may be expected to respond to the products of this invention. Other utilities of anti-progestational agents include treatment of fibrocystic disease of the breast. Certain cancers and in particular melanomas may respond favorably to corticoid/anticorticoid therapy.

The compounds according to the present invention may be administered to any warm-blooded mammal such as humans, domestic pets, and farm animals. Domestic pets include dogs, cats, etc. Farm animals include cows, horses, pigs, sheep, goats, etc.

The amount of active ingredient that may be combined with a carrier material to produce a single dosage form will vary depending upon the disease treated, the mammalian species, and the particular mode of administration. A therapeutically effective amount may be determined by routine experimentation and by analogy from the amounts used to treat the same disease states with analogous steroid compounds. For example, a unit dose of the steroid may preferably contain between 0.1 milligram and 1 gram of the active ingredient. A more preferred unit dose is between 0.001 and 0.5 grams. For the specific treatment of endometriosis or fibroids an amount of 0.01 to 10 mg/kg of body weight, preferably from 0.1 to 3 mg/kg may be administered. Similar dosages may be used for the other therapeutic purposes of these compounds. Ordinarily the compounds may be administered daily 1 to 4 times per day, preferably 1 to 2 times per day, but for uses such as for example in hormone replacement therapy, they may be administered in a cyclophasic regimen. In any case the frequency and timing of dosage will depend upon factors such as the half-life of the specific compound in the body, the dosage formulation and the route of administration. It will be understood, however, that the specific dose level for any particular patient will depend on a variety of factors including the activity of the specific compound employed; the age, body weight, general health, sex and diet of the individual being treated the time and route of administration; the rate of excretion: other drugs which have previously been administered; and the severity of the particular disease undergoing therapy, as is well understood by those of skill in the art.

Such compounds are useful in the treatment of endometriosis, uterine leiomyomas (fibroids) and certain cancers and tumors, in hormone replacement therapy as well as in the control of various steps in reproduction and fertility, such as contraception. A more detailed description of the potential uses of such compounds is given in Donaldson, Molly S.; Dorflinger, L.; Brown, Sarah S.; Benet, Leslie Z., Editors, *Clinical Applications of Mifepristone (RU 486) and Other Antiprogestins*, Committee on Antiprogestins: Assessing the Science, Institute of Medicine, National Academy Press, 1993.

The compounds of the present invention may be prepared by conventional methods known to those of ordinary skill of the art. By way of example the following general synthetic procedure is provided.

Compounds of this invention may be made according to the procedures outlined in Charts A–C (FIGS. 1–3), beginning with 3,3-[1,2-ethanediylbis(oxy)]-estra-5(10), 9(11) diene-17-one (A-1). This compound is converted to the 5(10)α-epoxide A-2 by a variety of methods, including preferably treatment of A-1 with $H_2O_2$, hexafluoroacetone and $Na_2HPO_4$ in $CH_2Cl_2$ and thence to the 11β-aryl compound A-3 by treatment with an aryl Grignard reagent mixed with a copper(1) salt, preferably CuCl (see Teutsch, G., et al., Steroids 59: 22–26 (1994)). Oxime formation with hydroxylamine hydrochloride in pyridine gives compound A-4 in excellent yield. Treatment of A-4 with N-bromosuccinimide (NBS) gives an intermediate 17-bromo-17-nitro compound, which is readily reduced by treatment with $NaBH_4$ to the 17-nitro compound A-5.

Michael (1,4) addition of the nitro compound in the presence of a base to α,β-unsaturated esters (method of Patchett, et al., J. Org. Chem., 27, 3822 (1962)) gives the corresponding adducts A-6. When for example methyl acrylate or methyl propiolate is used as the unsaturated ester, the adduct A-6 is formed with $R^7$ either $CH_2CH_2COOMe$ or CH=CHCOOMe, respectively. The adduct with methyl propiolate is mainly the E-isomer. Compounds of type A-5 or A-6 may be treated with mild acid (preferably trifluoroacetic acid and water in $CH_2Cl_2$) to form the dienones A-8. The group $R^7$ in compounds of type A-6 may be subjected to other reactions. Thus, ester groups may be reduced to primary alcohols with diisobutylaluminum hydride (DIBAL-H) to yield, for example, A-7 ($R^7$=$CH_2CH_2CH_2OH$) and A-7 ($R^7$=CH=CHCH$_2$OH), respectively. Acid treatment, preferably with trifluoroacetic acid and water in $CH_2Cl_2$, results in deketalization and dehydration to the corresponding dienones A-8.

When the aromatic ring of A-4 contains substituents that make the aryl ring particularly susceptible to electrophilic attack, such as for example N-dialkylamino or N-heterocycloalkyl, treatment with NBS results in bromination at the position ortho to the electron-donating substituent as well as conversion to the 17-bromo-17-nitro compound. The resulting aryl bromide may be carried through the rest of the procedures or the aryl bromine may be replaced by a hydrogen atom at any time before the final product A-8 is obtained by treating the appropriate compound with t-butyl lithium followed by a hydrogen ion source (see for example Kobrich and Buck, *J Amer. Chem. Soc.*, 103, 1412 (1970)). If tritium or deuterium compounds are used as the hydrogen ion source, an isotopically labeled compound is obtained, which is useful in tracer studies, such as for example metabolism, pharmacokinetics or receptor binding studies.

If it is not desired to have a halogenated aryl group, then the necessity for replacement of the bromine with hydrogen reduces the overall yield of the process. One of the findings of this invention is that if $R^1$ is an amino group such that $R^1$-Ar is a tertiary amine, the Ar ring can be deactivated towards substitution by first oxidizing the nitrogen to a tertiary amine N-oxide.

Therefore alternatively and preferably, when a tertiary amino substituent is present on the aromatic nucleus, the ring may be deactivated towards bromination by conversion of the tertiary amine to an amine oxide (A-4, $R^1$=$R_2N(O)$-). A number of oxidizing agents known to the art may be used. For example dimethyldioxirane gives excellent yields. Slightly lower yields are obtained by treatment with $H_2O_2$ and hexafluoroacetone, but the convenience of this latter procedure makes it generally preferable. The amine oxide is reduced back to the amine after the NBS reaction by simply shaking the reaction mixture with aqueous ferrous sulfate, which is normally used in the workup of the NBS reaction.

The resulting 17-bromo-17-nitro compound is then reduced to the 17-nitro compound A-5 by NaBH$_4$, just as previously noted. In the case of A-5 the 17-nitro substituent is primarily in the 17β-position, but either the α- or the β-compound may be used in the next step, as the anion generated in the Michael reaction equilibrates readily and the addition of unsaturated ester occurs from the α-side of the molecule.

Figure 2:
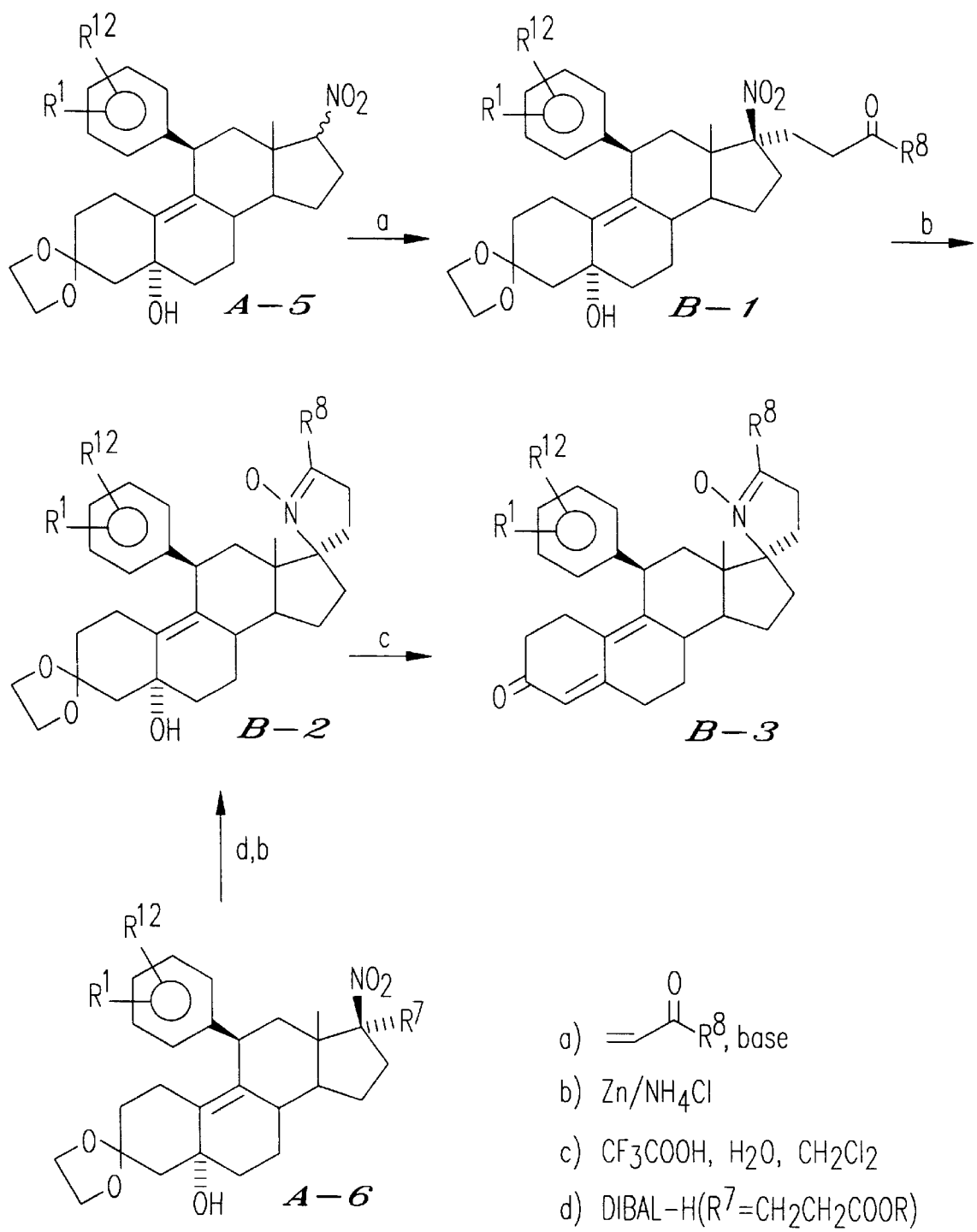
FIG. 2 illustrates the preparation of $C_{17}$ spirocyclic nitrone compounds.
Figure 3:
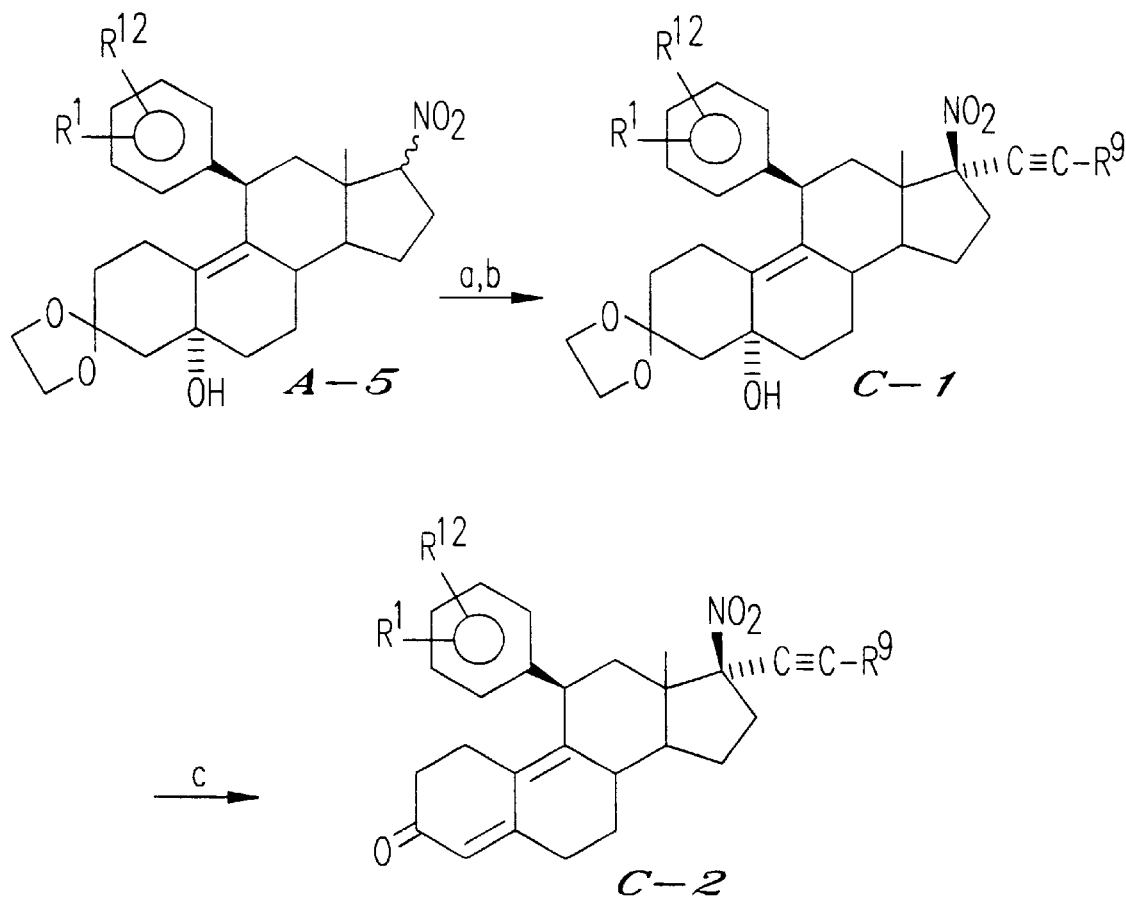
FIG. 3 illustrates the preparation of nitro alkynyl compounds.

When A-5 undergoes Michael addition to an α,β-unsaturated carbonyl compound, such as for example methyl vinyl ketone, as shown in FIG. 2, the resulting carbonyl product B-1 may be reduced and cyclized, for example by treatment with zinc and NH$_4$Cl, to form the nitrone B-2 (see method of Bonnett, et al., *J. Chem. Soc.*, 2094–2102 (1959)). If R$^{12}$ in B-2 is a bromine, the product may be reduced to B-2 (R$^{12}$=H) by the t-butyl lithium treatment previously described. Acid treatment of ketals B-2 leads to the dienones B-3. For example, if the α,β-unsaturated ketone is methyl vinyl ketone, the resulting final product is methyl nitrone B-3 (R$^8$=CH$_3$). The aldonitrones (B-2, R$^8$=H) are preferably made by reduction of ester A-6 (R$^7$=CH$_2$CH$_2$COOR) to the aldehyde (A-6 R$^7$=CH$_2$CH$_2$CHO) with limited DIBAL-H (see procedure of Miller, et al., J. Org. Chem., 24, 627 (1959)), followed by the zinc/NH$_4$Cl reduction and cyclization to nitrone B-2 (R=H) and deketalization/dehydration to the dienone B-3 (R$^8$=H).

17α-Carbon substituents may also be introduced into the nitro compound A-5 by means of alkynyl residues. For example when the anion of A-5 is treated in dimethylsulfoxide (DMSO) with an alkynyllead(IV) triacetate compound (procedure of Pinhey, J. T., et al., *J Chem. Soc. Perlin Trans.*, 1, 333 (1989)), the corresponding 17αalkynyl-17β-nitro compound C-1 (Chart C, FIG. 3) is obtained. Acid treatment as described above leads to the dienones C-2.

Having generally described this invention, a further understanding can be obtained by reference to certain specific examples which are provided herein for purposes of illustration only and are not intended to be limiting unless otherwise specified.

General Procedures. Unless otherwise stated, reagent-grade chemicals were obtained from commercial sources and were used without further purification. Ether and tetrahydrofuran (THF) were freshly distilled from sodium benzophenone ketyl pair under nitrogen. All moisture- and air-sensitive reactions and reagent transfers were carried out under dry nitrogen or argon. Thin layer chromatography (TLC) was performed on EM Science precoated silica gel 60 F-254 plates. Compounds were normally visualized by UV light (254 nm) p-anisaldehyde spray. Preparative column chromatography employed EM Science silica gel, 60 Å (230–400 mesh). Solutions were concentrated by use of a rotary evaporator under water aspirator pressure at ambient temperature. Melting points were taken on a Mel-Temp II and are uncorrected. Unless otherwise noted, $^1$H NMR spectra were obtained at 250 MHz on a Bruker AC 250 spectrometer in CDCl$_3$ as solvent with tetramethylsilane (TMS) as internal standard. Chemical shifts are reported in units of ppm downfield from TMS. Mass spectra were normally obtained by electron impact at 70 eV on a Hewlett Packard 5989A instrument. Elemental analyses were performed by Atlantic Microlab Inc., Atlanta, Ga.

EXAMPLE 1

Synthesis of 11β-[4-(N,N-Dimethylamino)phenyl]-17β-nitroestra-4,9-dien-3-one [A-8 (R$^1$=4-Me$_2$N, R$^7$=R$^{12}$=H)]

3,3-[1,2-Ethanediylbis(oxy)]-5α,10α-(oxido)estr-9(11)-en-17-one (A-2). To a solution of 32.0 g (102 mmol) of 3,3-[1,2-ethanediylbis(oxy)]estra-5(10),9(11)-dien-17-one in 192 mL of CH$_2$Cl$_2$ at 0° C. was added 7.04 mL (50.9 mmol) of hexafluoroacetone trihydrate (Lancaster Synthesis, Inc.) followed by 2.46 g (17.3 mmol) of Na$_2$HPO4, and then 8.64 mL (153 mmol) of 50% H$_2$O$_2$ was added dropwise to the efficiently stirred mixture (overhead mechanical stirring). Efficient stirring was continued for 18 h, during which time the temperature was allowed to gradually rise to room temperature, then 192 mL of saturated aqueous Na$_2$S$_2$O$_3$ was added. After stirring for 20 min, the mixture was combined with another (32.0 g) batch which had been prepared identically up to this point in parallel. The aqueous layer (bottom) was separated and extracted three times with 80 mL of EtOAc. The combined organic solution was diluted with 240 mL of EtOAc and washed twice with 80 mL of saturated aqueous NaHCO$_3$, twice with 80 mL of brine, dried over MgSO4, filtered, and the solvent was removed under reduced pressure. The yellow solid (76.1 g) was triturated with 320 mL of diethyl ether with magnetic stirring for 12 h in a closed flask. The resulting white slurry was combined with three other batches (3×32.0 g) which had been prepared identically (and proportionally) to this point, in parallel, then suction filtered through a coarse-porosity sintered glass funnel, rinsing three times with 40 mL of diethyl ether, then allowed to suck dry for 1.5 h. The resulting white filter cake was gently scraped into a fine white powder and dried in vacuo to afford epoxide A-2 (89.5 g, 53% yield). $^1$H NMR (250 MHz, CDCl$_3$) δ 6.06 (br s, 1), 3.98–3.88 (m, 4), 2.52–2.44 (m, 2), 1.32–1.12 (m, 1), 0.88 (s, 3).

11β-[4-(N,N-Dimethylamino)phenyl]-3,3-[1,2-ethanediylbis(oxy)]α-hydroxyestra-9-ene-17-one [A-3 (R$^1$=4-Me$_2$N—, R$^{12}$=H)]. A flask equipped with an overhead mechanical stirrer and charged with 11.6 g (475 mmol) of magnesium turnings was flame-dried under a stream of dry nitrogen. After cooling to room temperature, 400 mL of THF was added, followed by a few crystals of iodine, thus imparting a light brown coloration. To the efficiently stirred mixture was added 35 mL of a solution of 91.4 g (457 mmol) of 4-bromo-N,N-dimethylaniline in 400 mL of THF. After heating the mixture to reflux for ca. 5 min, the iodine color quickly faded to colorless, at which time the mixture was allowed to cool to room temperature. The remainder of the bromide solution was added dropwise over a period of 2 h. The mixture was then cooled in an ice-water bath for 1.8 h, then 18.1 g (183 mmol) of finely powdered CuCl was added in one portion. After the mixture was stirred efficiently for 60 sec, a solution of 60.4 g (183 mmol) of A-2 in 453 mL of THF was added (poured in) over 25 sec, causing the formation of a voluminous light yellow precipitate. After 15 min, 300 mL of saturated aqueous NH$_4$Cl was slowly added, followed by 755 mL of EtOAc. After stirring for 10 min, the aqueous layer was separated and extracted three times with 300 mL of EtOAc. The combined organic solution was washed eight times with 300 mL of brine (until the brine washings were relatively low in opacity), dried over MgSO$_4$, filtered, and the solvent was removed under reduced pressure. The black viscous oil was taken up in 30 mL of CH$_2$Cl$_2$ and chromatographed on silica gel (elution of aniline reagent by-product with CH$_2$Cl$_2$, then elution of product with EtOAc) to afford adduct A-3 (R$^1$=4-Me$_2$N—, R$^{12}$=H) (75.4 g, 91% yield). $^1$H NMR (250 MHz, CDCl$_3$) δ 7.06 (d, 2, J=8.3 Hz), 6.64 (d, 2, J=8.8 Hz), 4.37 (s, 1), 4.24 (d, 1, J=7.3 Hz), 4.02–3.90 (m, 4), 2.91 (s, 6), 0.52 (s, 3).

11β-[4-(N,N-Dimethylamino)phenyl]-3,3-[1,2-ethanediylbis(oxy)]-5α-hydroxyestr-9-en-17-oxime [A-4 (R$^1$=4-Me$_2$N—, R$^{12}$=H)]. To a solution of 44.3 g (98.1 mmol) of ketone A-3 ($R^1$=4-$Me_2N$—, $R^{12}$=H) in 333 mL of anhydrous pyridine at room temperature under nitrogen was added 11.3 g (162 mmol) of hydroxylamine hydrochloride. After stirring for 17 h, 1.10 L of water and 333 mL of EtOAc were added. After stirring for 10 min, the aqueous layer was separated and extracted three times with 160 mL of EtOAc. The combined organic solution was washed twice with brine, dried over $Na_2SO_4$, filtered, and the solvent was removed under reduced pressure. The resulting foam was iteratively rotary evaporated under reduced pressure three times with 160 mL of toluene at 40° C. Further solvent was removed in vacuo, thus affording a brown foam (48.4 g) free of pyridine by $^1H$ NMR analysis. The material could be carried on without further purification. $^1H$ NMR (250 MHz, $CDCl_3$) δ 8.62 (br s, 1), 7.07 (d, 2, J=9.4 Hz), 6.63 (d, 2, J=9.0 Hz), 4.38 (s, 1), 422 (d, 1, J=6.6 Hz), 4.03–3.88 (m, 4), 2.89 (s, 6), 0.56 (s, 3).

11β-[4-(N,N-Dimethyl-N-(oxy)amino)phenyl]-3,3-[1,2-ethanediylbis(oxy)]-5α-hydroxyestr-9-en-17-oxime [A-4 ($R^1$=4-$Me_2N(O)$—, $R^{12}$=H). To a solution of 6.16 g (13.2 mmol) of A-4 ($R^1$=4-$Me_2N$—, $R^{12}$=H) in 26 mL of $CH_2Cl_2$ at 0° C. was added 0.92 mL (6.60 mmol) of hexafluoroacetone trihydrate. With vigorous stirring, 1.60 mL (27.7 mmol) of 50% $H_2O_2$ was added dropwise. After 5 h of stirring vigorously at 0° C., the resulting red mixture was diluted with EtOAc and water. The aqueous layer was separated and extracted three times with EtOAc. The water layer was concentrated under reduced pressure to afford amine oxide A-4 ($R^1$=4-$Me_2N(O)$—, $R^{12}$=H) as a white solid (5.31 g, 83% yield). $^1H$ NMR (250 MHz, $CDCl_3$) δ 11.01 (br s, 1), 7.89, 7.35 (ABq, 4, J=8.7 Hz), 4.42 (br s, 1), 4.33 (d, 1, J=6.9 Hz), 4.05–3.89 (m, 4), 3.65 (s, 3), 3.64 (s, 3), 2.61–1.01 (m, 18), 0.483 (s, 3).

17-Bromo-11β-[4-(N,N-dimethylamino)phenyl]-3,3-[1,2-ethanediylbis(oxy)]-5α-hydroxy-17-nitroestr-9-ene. To a solution of 4.39 g (24.7 mmol) of NBS in 20 mL of 1,4-dioxane and 20 mL of water at room temperature was added a solution of 2.47 g (24.7 mmol) of $KHCO_3$ in 20 mL of water. After 5 min, 4.60 g (9.86 mmol) of oxime A-4 ($R^1$=4-$Me_2N(O)$—, $R^{12}$=H) in 35 mL of 1,4-dioxane and 20 mL of water was added over 5 min, causing a lime-green/yellow coloration which gradually faded to yellow. After 16 h, freshly prepared saturated aqueous $FeSO_4$ (120 mL) was added, causing a brown precipitate. After stirring vigorously for 15 min, the mixture was extracted three times with EtOAc. The combined organic solutions were washed three times with freshly prepared saturated aqueous $FeSO_4$, twice with brine, dried over $Na_2SO_4$, filtered, and the solvent was removed under reduced pressure to afford 17-bromo-11β-[4-(N,N-dimethylamino)phenyl]-3,3-[1,2ethanediylbis(oxy)-5α-hydroxy-17-nitroestr-9-ene as a yellow-brown foam (5.57 g), which was used directly in the next step without further purification.

11β-[4-(N,N-Dimethylamino)phenyl]-3,3-[1,2-ethanediylbis(oxy)]-5α-hydroxy-17-nitroestr-9-ene [A-5 ($R^1$=4-$Me_2N$—, $R^{12}$=H)]. To a solution of 5.57 g (9.61 mmol) of the above 17-bromo-17-nitro alcohol in 102 mL of THF and 20 mL of water at room temperature was added 1.21 g (31.8 mmol) of $NaBH_4$ in several portions, each time ensuing a vigorous gas evolution. After 2 h, a solution of 7.01 g (101 mmol) of hydroxylamine hydrochloride in 175 mL of water was carefully added followed by addition of EtOAc. After stirring for 20 min, the mixture was extracted three times with EtOAc. The combined organic solutions were washed three times with water, once with saturated aq $NaHCO_3$, and once with brine, dried over $Na_2SO_4$, filtered, and the solvent was removed under reduced pressure. The resulting foam was taken up in a minimal amount of $CH_2Cl_2$ and chromatographed on silica gel (50% EtOAc in hexanes) to afford nitro intermediate A-5 ($R^1$=4-$Me_2N$—, $R^{12}$=H) (2.39 g, 50% yield for 3 steps) as a yellow solid. $^1H$ NMR (250 MHz, $CDCl_3$) δ 7.03, 6.63 (ABq, 4, J=8.8 Hz), 4.39 (s, 1), 4.39–4.30 (m, 1), 4.23 (d, 1, J=7.0 Hz), 4.02–3.93 (m, 4), 2.90 (s, 6), 0.372 (s, 3).

11β-[4-(N,N-Dimethylamino)phenyl]-17β-nitroestra-4,9-dien-3-one [A-8 ($R^1$=4-$Me_2N$, $R^7$=$R^{12}$=H)]. To a rapidly stirred mixture of 300 mg (0.622 mmol) of nitro intermediate A-6 ($R^1$=4-$Me_2N$—, $R^7$=$R^{12}$=H), 10 mL of $CH_2Cl_2$, and 0.56 mL of water at 0° C. was added dropwise 0.84 mL (10.9 mmol) of trifluoroacetic acid (TFA). After stirring vigorously for 45 min, the mixture was stirred with saturated aqueous $NaHCO_3$ for 1.5 h. The aqueous layer was separated and extracted three times with EtOAc. The combined organic solution was washed three times with saturated aqueous $NaHCO_3$, twice with brine, dried over $Na_2SO_4$, filtered, and the solvent was removed under reduced pressure. Chromatography on silica gel (45% EtOAc in hexanes) afforded A-8 ($R^1$=4-$Me_2N$—, $R^7$=$R^{12}$=H) (235 mg, 90% yield) as an off-white foam. Two triturations of a sample of this material with methanol and concentration of the resulting methanol solutions afforded a sample of >97% purity (by HPLC analysis). $^1H$ NMR (250 MHz, $CDCl_3$) δ 7.00, 6.64 (ABq, 4, J=8.6 Hz), 5.77 (s, 1), 4.42–4.33 (m, 2), 2.91 (s, 6), 0.446 (s, 3). MS m/z (rel inten) 420 ($M^+$, 27), 121 (100). Anal. Calcd. for $C_{26}H_{32}N_2O_3 \cdot 0.25 H_2O$: C, 73.47; H, 7.71; N, 6.59. Found: C, 73.11; H, 7.61; N, 6.55.

EXAMPLE 2

Synthesis of 11β-[4-(N,N-Dimethylamino)phenyl]-17α-(3-hydroxypropyl)-17β-nitroestra-4,9-dien-3-one [A-8 ($R^1$=4-$Me_2N$, $R^7$=—$(CH_2)_3OH$, $R^{12}$=H)]

11β-[3-Bromo-4-(N,N-dimethylamino)phenyl]-3,3-[1,2-ethanediylbis(oxy)]-5α-hydroxy-17-nitroestr-9-ene [A-5 ($R^1$=4-$Me_2N$—, $R^{12}$=3-Br). To a vigorously stirred suspension of 1.28 g of finely powdered N-bromosuccinimide in 5 mL of water and 5 mL of dioxane was added a solution of 1.07 g of sodium bicarbonate in 5 mL of water. To the resulting suspension was added 1.28 g of oxime A-4 ($R^1$=4-$Me_2N$—, $R^{12}$=H) in 10 mL of dioxane. The resulting suspension was stirred for two days at the end of which an oil separated out. Water was added to the reaction mixture followed by extraction with ether. The ether layer was washed with water followed by dilute ferrous sulfate solution, and concentrated under reduced pressure. The crude product was dissolved in 18 mL of THF and 3.5 mL of water. Sodium borohydride (350 mg) was added over a period of 15 min. After sturing for an hour at room temperature an additional 150 mg of borohydride was added. The reaction was stirred for an additional 1.5 h and then brought to pH 7 with hydroxylamine hydrochloride in water. The mixture was extracted with ether, the ether layer washed, dried, filtered and concentrated to give 1.3 g of crude product. This material was chromatographed on silica gel using 2:1 hexane-ethyl acetate to give 325 mg of A-5 ($R^1$=4-$Me_2N$—, $R^{12}$=3-Br) as a white solid (47% yield). IR 3680, 3005, 2860, 1595, 1535, 1412, 1379, 1345, 1109, 836 $cm^{-1}$; $^1H$ NMR (250 MHz, $CDCl_3$) δ 0.38 (s, 3, $C_{18}$ H), 2.91 (s, 6, $N(CH_3)_2$), 3.99 (m, 4, $O(CH_2)_2O$), 4.12 (d, 1, $C_{11α}$ H), 4.31 (t, 1, $C_{17α}$ H), 4.42 (s, 1, $C_5OH$), 6.88–7.37 (m, 3, 11β-[3-Bromo-17α-(2-carbomethoxyethyl)-4-(N,N-dimethylamino)phenyl]-3,3-[1,2-ethanediylbis(oxy)]-5α-hydroxy-17β-nitroestr-9-ene [A-6 ($R^1$=4-$Me_2N$—, $R^7$=—$(CH_2)_2COOMe$, $R^{12}$=3-Br). To a suspension of 1.5 g of the nitro compound A-5 ($R^1$=4-$Me_2N$—, $R^{12}$3-Br) in 8.0 mL of t-butanol and 15 mL of methyl acrylate was added 1.5 mL of Triton B. The mixture was stirred at room temperature overnight and then quenched by pouring in ice-cold water. This was extracted thrice with ether, washed with saturated ammonium chloride and dried over anhydrous magnesium sulfate to give 1.2 g (88% yield) of A-6 ($R^1$=4-$Me_2$N—, $R^7$=—($CH_2$)$_2$COOMe, $R^{12}$=3-Br). $^1$H NMR (250 MHZ, CDCl$_3$); δ 7.36 (s, 1, ArH), 6.95 (d, 1, J=8.4 Hz, ArH), 7.09 (d, 1, J=8.4 Hz, C$_5$ ArH), 4.36 (s, 1, C$_5$OH), 4.29 (d, 1, J=6.5 Hz, C$_{11\alpha}$ H), 3.95 (m, 4, (OCH$_2$)$_2$), 3.68 (s, 3, CO$_2$CH$_3$), 2.90 (s, 6, N(CH$_3$)$_2$), 0.39 (s, 3, C$_{18}$ H).

11β-[3-Bromo-4-(N,N-dimethylamino)phenyl]-3,3-[1,2-ethanediylbis(oxy)]-5α-hydroxy-17α-(3-hydroxypropyl)-17β-nitroestr-9-ene [A-7 ($R^1$=$Me_2$N—, $R^7$=—($CH_2$)$_3$OH, $R^{12}$=3-Br)]. To a solution of 1.14 mg (1.75 mmol) of A-6 ($R^1$=4-$Me_2$N—, $R^7$=—($CH_2$)$_2$COOMe, $R^{12}$=3-Br) in 6.3 mL of toluene was added 5.23 mL of a 1 M solution of diisobutyl aluminum hydride (DIBAL-H) in hexane dropwise at room temperature. During the course of the addition the temperature rose to 45° C. and was maintained at this temperature for an additional 2 h after addition. The reaction was quenched by adding 0.63 mL of methanol in 0.93 mL of toluene followed by 0.26 mL of water and 0.27 mL of methanol. The mixture was stirred for 30 min and then filtered through Celite and concentrated under reduced pressure. The crude product was purified by chromatography on silica gel using 5% acetone in dichloromethane as eluent to give 945 mg (87% yield) of A-7 ($R^1$=4-$Me_2$N—, $R^7$=—(CH$_2$)$_3$OH, $R^{12}$=3-Br). $^1$H NMR (CDCl$_3$) δ 0.39 (s, 3, C$_{18}$H), 2.76 (s, 6, N(CH$_3$)$_2$), 3.61–3.68 (m, 2, CH$_2$OH), 3.95 (m, 4, O(CH$_2$)$_2$O), 4.28 (d, 1, 11$_\alpha$ H), 4.42 (s, 1, C$_5$ OH), 6.88–7.37 (m, 3, ArH).

11β-[4-(N,N-Dimethylamino)phenyl]-3,3-[1,2-ethanediylbis(oxy)]-5α-hydroxy-17α-(3hydroxypropyl)-17β-nitroestr-9-ene [A-7 ($R^1$=$Me_2$N—, $R^7$=—($CH_2$)$_3$OH, $R^{12}$=H)]. To a solution of 615 mg (1.09 mmol) of A-7 ($R^1$=$Me_2$N—, $R^7$=—($CH_2$)$_3$OH, $R^{12}$=3-Br) dissolved in 50 mL of THF at −78° C. under an inert atmosphere was added 3.0 mL of 1.7 M t-butyllithium at −78° C. over a period of 30 min. This resulted in a bright yellow solution that was stirred at −78° C. for 10–15 min. The reaction mixture was quenched with saturated ammonium chloride, extracted with ethyl acetate, washed with water followed by brine and dried over anhydrous magnesium sulfate. The dried solution was filtered, concentrated in vacuum and the crude product chromatographed on silica gel with 10:3:2 hexane-EtOAc-Et$_2$O to give 270 mg (49% yield) of pure A-7 ($R^1$=$Me_2$N—, $R^7$=—(CH$_2$)$_3$ OH, $R^{12}$=H). $^1$H NMR (250 MHz, CDCl$_3$); δ 7.00 (d, 2, J=8.6 Hz, ArH), 6.59 (d, 2, J=8.8 Hz, ArH), 4.37 (s, 1, C$_5$OH), 4.25 (d, 1, J=6.3 Hz, C$_{11\alpha}$ H), 3.88–3.98 (m, 4, (OCH$_2$)$_2$), 3.49–3.70 (m, 2, CH$_2$OH), 2.88 (s, 6, N(CH$_3$)$_2$), 0.34 (s, 3, C$_{18}$ H).

11β-[4-(N,N-Dimethylamino)phenyl]-17α-(3-hydroxypropyl)-17β-nitroestra-4,9-dien-3-one [A-8 ($R^1$=4-$Me_2$N—, $R^7$=—($CH_2$)$_3$OH, $R^{12}$=h)]. A solution of 270 mg (0.5 mmol) of A-7 ($R^1$=4-$Me_2$N—, $R^7$=—($CH_2$)$_3$OH, $R^{12}$=H) in 25 mL of CH$_2$Cl$_2$ was cooled to 0° C. To this was added 0.5 mL of water followed by 1.5 mL of TFA dropwise. The reaction mixture turned bright yellow. After stirring for 1 h at 0° C. the reaction was quenched with sat. NaHCO$_3$ and extracted with 200 mL of CH$_2$Cl$_2$. The organic layer was washed with water, followed by brine and dried over anhydrous MgSO4. The CH$_2$Cl$_2$ layer was filtered, concentrated and the residue chromatographed on silica gel using 10% acetone in CH$_2$Cl$_2$ to give 167 mg (70% yield) of desired dienone A-8 ($R^1$=4-$Me_2$N—, $R^7$=—($CH_2$)$_3$OH, $R^{12}$=H). Preparative HPLC purification was employed on a YMC C-18 reverse phase column using 80% methanol water to get greater than 97% pure material: $^1$H NMR (250 MHz, CDCl$_3$) δ 6.99 (d, 2, J=8.6 Hz, ArH), 6.63 (d, 2, J=8.9 Hz, ArH), 5.77 (s, 1, C$_4$H), 4.40 (d, 1, J=6.5 Hz, C$_{11\alpha}$ H), 3.63–3.74 (m, 2, CH$_2$OH), 2.90 (s, 6, N(CH$_3$)$_2$), 0.45 (s, 3, C$_{18}$ H); mass spectrum, m/z (rel intensity) 478 (14), 428 (27), 147 (8), 121 (100), 91 (10); Exact mass; Calcd for C$_{29}$H$_{38}$N$_2$O$_4$: 478.2831. Found: 478.2837; Anal. Calcd for C$_{29}$H$_{38}$N$_2$O$_4$.H$_2$O: C, 70.13; H, 8.12; N, 5.64. Found: C, 69.72; H, 8.01; N, 5.00.

EXAMPLE 3

Alternate Synthesis of 11β-[4-(N,N-Dimethylamino)phenyl]17a-(3-hydroxypropyl)-17α-(3hydroxypropyl)-17β-nitroestra-4,9-dein-3-one [A-8 ($R^1$=4-$Me_2$N—, $R^7$=—(CH$_2$)$_3$OH, $R^{12}$=H)]

17α-(2-Carbomethoxyethyl)-11β-[4-(N,N-dimethylamino)phenyl]-3,3-[1,2-ethanediylbis(oxy)]-5α-hydroxy-17β-nitroestr-9-ene [A-6 ($R^1$=4-$Me_2$N—, $R^7$=—(CH$_2$)$_2$COOMe, $R^{12}$=H)]. To a solution of 1.5 g (0.047 mmol) of A-5 ($R^1$4-$Me_2$N—, $R^{12}$=H) in 8.3 mL of t-butanol was added 16.5 mL of methyl acrylate. To this was then added 1.5 mL of a solution of Triton B in methanol. The reaction mixture was stirred for 2 h and then poured into ice cold water and extracted with ethyl acetate. The organic layer was washed with water followed by brine, dried over anhydrous magnesium sulfate, filtered and concentrated under vacuum. The crude product was chromatographed on silica gel with 2:1 hexane-ethyl acetate as eluent to give 1.56 g (88% yield) of A-6 ($R^1$=4-$Me_2$N—, $R^7$=—(CH$_2$)$_2$COOMe, $R^{12}$=H). $^1$H NMR (250 MHz, CDCl$_3$); δ 0.39 (s, 3, C$_{18}$ H), 2.90 (s, 6, N(CH$_3$)$_2$), 3.68 (s, 3, CO$_2$CH$_3$), 3.95 (m, 4, O(CH$_2$)$_2$), 4.29 (d, 1, C$_{11\alpha}$ H), 4.36 (s, 1, C$_5$ OH), 6.63 (d, 2, ArH), 7.03 (d, 2, ArH).

11β-[4-(N,N-Dimethylamino)phenyl]-3,3-[1,2-ethanediylbis(oxy)]-5α-hydroxy-17α-(3hydroxypropyl)-17β-nitroestr-9-ene [A-7 ($R^1$=4-$Me_2$N—, $R^7$=—(CH$_2$)$_3$OH, $R^{12}$=H)]. To 83 mg (0.147 mmol) of A-6 ($R^1$=4-$Me_2$N—, $R^7$=—(CH$_2$)$_2$COOMe, $R^{12}$=H) dissolved in 3 mL of toluene and maintained under an atmosphere of nitrogen was added dropwise 0.44 mL of a 1 M solution of DIBAL-H in hexane. During the addition, the temperature rose to about 45° C. The reaction mixture was maintained at 45° C. for 2 h. The reaction was quenched by adding 0.2 mL of methanol in 0.5 mL of toluene followed by addition of 0.1 mL of water in 0.3 mnL of methanol. This was then filtered through celite and concentrated. The crude product was chromatographed on silica gel using 5% acetone in dichloromethane to give 70 mg of white solid. $^1$H NMR (250 MHz, CDCl$_3$) δ 0.39 (s, 3, C$_{18}$ H), 2.86 (s, 6, N(CH$_3$)$_2$), 3.61–3.64 (m, 2, CH$_2$OH), 3.95 (m, 4, O(CH$_2$)$_2$)$_2$), 4.28 (d, 1, C$_{11\alpha}$ H), 4.42 (s, 1, C$_5$OH), 6.63 (d, 2, ArH), 7.03 (d, 2, ArH).

11β-[4-(N,N-Dimethylamino)phenyl]-17α-(3-hydroxypropyl)-17β-nitroestra-4,9-dien-3-one [A-8 ($R^1$=4-$Me_2$N—, $R^7$=—(CH$_2$)$_3$OH, $R^{12}$=H)]. To a solution of 70 mg (0.12 mol) of A-7 ($R^1$=4-$Me_2$N—, $R^7$=—(CH$_2$)$_3$OH, $R^{12}$=H) in 1 mL of acetone was added a catalytic amount of p-toluenesulfonic acid at −10° C. The reaction was slowly warmed to ambient temperature and stirred for an additional 3 h. The reaction was quenched with saturated sodium bicarbonate, extracted with methylene chloride and the organic layer washed with water followed by brine. The methylene chloride layer was then dried over anhydrous magnesium sulfate, filtered and concentrated. The crude product was chromatographed on silica gel with 5% acetone in dichloromethane as eluent to give 35 mg of A-8 ($R^1$=4-$Me_2$N—, $R^7$=—(CH$_2$)$_3$OH, $R^{12}$=H) in about 50% yield. $^1$H NMR (250 MHz, CDCl$_3$); same as shown for example 2.

EXAMPLE 4

Synthesis of 11β-[4-(N,N-Dimethylamino)phenyl]-17α-[1-(3-hydroxy)-propenyl]-17-nitroestra-4,9-dien-3-one [A-8 ($R^1$=4-$Me_2$N—, $R^7$= $HOCH_2$CH═CH—, $R^{12}$=H)].

11β-[3-Bromo-17α-(2-(E)-carbomethoxyethenyl)-3,3-4-(N,N-dimethylamino)phenyl]-[1,2-ethanediylbis(oxy)]-5α-hydroxy-17β-nitroestr-9-ene [A-6 ($R^1$=4-$Me_2$N—, $R^7$=(E)—CH═CHCOOMe, $R^{12}$=3-Br)]. A solution of 3.14 g (5.6 mmol) of A-5 ($R^1$=4-$Me_2$N—, $R^{12}$=3-Br), 1.632 g (28.0 mmol) of KF and 1.821 g (5.6 mmol) of n-$Bu_4$NBr in 12.5 mL of DMSO was stirred for 30 min at room temperature. Then 1.0 mL (11.2 mmol) of methyl propiolate was added dropwise and the solution was stirred for 1 h. The reaction mixture was diluted with water and extracted with ethyl acetate. The organic layer was washed with water, followed by brine and dried over anhydrous $MgSO_4$. The organic layer was filtered, concentrated, and the crude product chromatographed on silica gel using 1:1 hexane-ethyl acetate to give 2.02 g of pure E-isomer, 0.6 g of pure Z-isomer and 0.40 g of a mixture of isomers in an overall 85% yield of A-6 ($R^1$=4-$Me_2$N—, $R^7$=—CH═CHCOOMe, $R^{12}$=H). The E-isomer has the following spectral data: $^1$H NMR (250 MHz, $CDCl_3$) δ 7.36 (d, 1, J=15.9 Hz, CH═CHCO$_2$Me), 7.35 (s, 1, ArH), 7.08 J=8.6 Hz, ArH), 6.96 (d, 1, J=8.6 Hz, ArH), 5.87 (d, 1, J=15.9 Hz, CH═CHCO$_2$Me), 4.46 (s, 1, C$_5$ OH), 4.21 (d, 1, J=7.0 Hz, C$_{11α}$ H), 3.93–4.02 (m, 4, (OCH$_2$)$_2$), 3.80 (s, 3, CO$_2$CH$_3$), 2.76 (s, 6, N(CH$_3$)$_2$), 0.49 (s, 3, C$_{18}$ H). The Z-isomer has the following spectral data: $^1$H NMR (250 MHz, CDCl$_3$) δ 7.32 (s, 1, ArH), 7.05 (d, 1, J=8.6 Hz, ArH), 6.94 (d, 1, J=8.2 Hz, ArH), 6.58 (d, 1, J=12.7 Hz, CH═CHCO$_2$Me), 6.05 (d, 1, J=12.3 Hz, CH═CHCO$_2$Me), 4.46 (s, 1, C$_5$OH), 4.31 (d, 1, J=7.0 Hz, C$_{11α}$H), 3.96–4.02 (m, 4, (OCH$_2$)$_2$), 3.68 (s, 3, CO$_2$CH$_3$), 2.75 (s, 6, N(CH$_3$)$_2$), 0.44 (s, 3, C$_{18}$H).

11β-[3-Bromo-4-(N,N-dimethylamino)phenyl]-3,3-[1,2-ethanediylbis(oxy)]-5α-hydroxy-17α-[(E)-1-(3-hydroxy)propenyl]-17β-nitroestr-9-ene [A-7 ($R^1$=4-$Me_2$N—, $R^7$=(E)—CH═CHCH$_2$OH, $R^{12}$=3-Br)]. To a solution of 2.025 g (3.14 mmol) of A-6 ($R^1$=4-$Me_2$N—, $R^7$=(E)—CH═CHCOOMe, $R^{12}$=3-Br) dissolved in 25 mL of CH$_2$Cl$_2$ maintained under an atmosphere of nitrogen at 78° C. was added 12.96 mL of a 1 M solution of DIBAL-H in hexane dropwise. The reaction mixture was slowly warmed to room temperature and stirred for 1 h. The reaction was quenched by adding 5 mL of methanol, followed by saturated Rochelle's salt solution and ethyl acetate. This mixture was stirred until no more precipitate was seen. The organic layer was washed with water, followed by brine, dried over anhydrous MgSO$_4$ and then filtered. The filtrate was concentrated and the crude product was chromatographed on silica gel using 5% acetone in dichloromethane to give 1.40 g (72% yield) of alcohol A-7 ($R^1$=4-$Me_2$N—, $R^7$=(E)—CH═CHCH$_2$OH, $R^{12}$=3-Br). $^1$H NMR (250 MHz, CDCl$_3$) δ 7.36 (s, 1, ArH), 7.08 (d, 1, J=8.4 Hz, ArH), 6.95 (d, 1, J=8.2 Hz, ArH), 6.58 (d, 1, J=15.9 Hz, CH═CHCH$_2$OH), 5.80 (dt, 1, Jl =4.37 Hz J$_2$=15.5 Hz, CH═CHCH$_2$OH), 4.49 (s, 1, C$_5$OH), 4.20–4.26 (br d, 3, CH$_2$OH, C$_{11α}$ H), 3.92–4.02 (m, 4, (OCH$_2$)$_2$), 3.68 (s, 3, CO$_2$CH$_3$), 2.75 (s, 6, N(CH$_3$)$_2$), 0.46 (s, 3, C$_{18}$H).

11β-[4-(N,N-Dimethylamino)phenyl]-3,3-[1,2-ethanediylbis(oxy)]-5α-hydroxy-17α-[(E)-1-(3-hydroxy)propenyl]-17β-nitroestr-9-ene [A-7 ($R^1$=4-$Me_2$N—, $R^7$=(E)—CH═CHCH$_2$OH, $R^{12}$=H)]. To a solution of 1.40 g (2.27 mmol) of A-7 ($R^1$=4-$Me_2$N—, $R^7$=(E)—CH═CHCH$_2$OH, $R^{12}$=3-Br), dissolved in 100 mL of THF at −78° C. under argon was added 5.5 mL of a 1.7 M solution of t-butyllithium at −78° C. over 10 min. The reaction mixture was quenched with saturated ammonium chloride, extracted with ethyl acetate, washed with water followed by brine and dried over anhydrous magnesium sulfate. The dried solution was then filtered, concentrated in vacuum and the crude product was used without further purification in the next step. $^1$H NMR (250 MHz, CDCl$_3$) δ 7.04 (d, 2, J=8.8 Hz, ArH), 6.64 (d, 2, J=8.8 Hz, ArH), 6.58 (d, 1, J=15.9 Hz, CH═CHCH$_2$OH), 5.80 (dt 1, J$_1$=4.7 Hz, J$_2$=15.5 Hz, CH═CHCH$_2$OH), 4.45 (s, 1, C$_5$OH), 4.27 (d, 2, J=4.0 Hz, CH$_2$OH), 4.27 (d, 1, J=7.4 Hz, C$_{11α}$H), 3.90–4.02 (m, 4, (OCH$_2$)$_2$), 2.90 (s, 6, N(CH$_3$)$_2$), 0.46 (s, 3, C$_{18}$H).

11β-[4-(N,N-Dimethylamino)phenyl]-17α-[(E)-1-(3-hydroxy)propenyl]-17β-nitroestra-4,9-dien-3-one, [A-8 ($R^1$=4-$Me_2$N—, $R^7$=(E)—CH═CHCH$_2$OH, $R^{12}$=H)]. A solution of 1.08 g (0.5 mmol) of crude A-7 ($R^1$=4-$Me_2$N—, $R^7$=(E)—CH═CHCH$_2$OH, $R^{12}$=H), in 25 mL of CH$_2$Cl$_2$ was cooled to 0° C. To this was added 1.0 mL of water followed by 5.0 mL of TFA dropwise. The reaction mixture turned bright yellow. After stirring for 1 h at 0° C. the reaction was quenched with sat. NaHCO$_3$ and extracted with 250 mL of CH$_2$Cl$_2$. The organic layer was washed with water, followed by brine and dried over anhydrous MgSO$_4$. The dried solution was filtered, concentrated and the crude product chromatographed on silica gel using 10% acetone in CH$_2$Cl$_2$ to give 515 mg of desired dienone A-8 ($R^1$=4-$Me_2$N—, $R^7$=(E)—CH═CHCH$_2$OH, $R^{12}$=H) in 50% yield. Preparative HPLC purification was employed on a YMC C-18 reverse phase column using 80% methanol water to get greater than 97% pure material: $^1$H NMR (250 MHz, CDCl$_3$) δ 6.99 (d, 2, J=8.6 Hz, ArH), 6.64 (d, 2, J=8.8 Hz, ArH), 6.30 (d, 1, J=16.0 Hz, CH═CHCH$_2$OH), 5.83 (dt, 1, J$_1$=4.7 Hz, J$_2$=15.5 Hz, CH═CHCH$_2$OH), 5.76 (s, 1, C$_4$H), 4.34–4.28 (br d, 3, CH$_2$OH, C$_{11α}$ H), 2.90 (s, 6, N(CH$_3$)$_2$), 0.53 (s, 3, C$_{18}$ H); mass spectrum, m/z (rel intensity) 476(9), 429(16), 415(18), 143(17), 121(100); Exact mass: Calcd. for C$_{29}$H$_{38}$N$_2$O$_4$: 478.2831. Found: 478.2837; Anal. Calcd. for C$_{29}$H$_{36}$N$_2$O$_4$.0.25 H$_2$O: C, 73.54; H, 7.99; N, 5.62. Found: C, 73.31; H, 8.31; N, 4.96.

EXAMPLE 5

Synthesis of 11β-(4-Acetylphenyl)-17α-(3-hydroxypropyl)-17β-nitro estra-4,9-dien-3-one [A-8 ($R^1$=4-CH$_3$C(O)—, $R^7$=—(CH$_2$)$_3$OH, $R^{12}$=H)].

4-Bromoacetophenone ethylene ketal. A well-stirred mixture of 25.0 g (126 mmol) of p-bromoacetophenone, 70.0 mL (1.26 mol) of ethylene glycol, and 2.38 g (12.5 mmol) of p-TsOH in 350 mL of toluene was heated to reflux in a Dean-Stark apparatus. After 22 h, the mixture was allowed to cool to ambient temperature, saturated aq NaHCO$_3$ was carefully added, and the mixture was extracted with ether. The combined organic solutions were washed with water and brine, dried over MgSO$_4$, filtered, and the solvent was removed under reduced pressure. The resulting solid was dried in vacuo at ambient temperature to afford 4-bromoacetophenone ethylene ketal (30.2 g, 99% yield) as an off-white solid, which was used without ftirther purification. $^1$H NMR (250 MHz, CDCl$_3$) δ 7.46 (m, 2), 7.36 (m, 2), 4.03 (m, 2), 3.77 (m, 2), 1.63 (s, 3).

3,3-[1,2-Ethanediylbis(oxy)]-11β-{4-{1,1-[1,2-ethanediylbis(oxy)]ethyl}phenyl}-5α-hydroxyestr-9-en-17-one [A-3 ($R^1$=4-CH$_3$C(OCH$_2$)$_2$—, $R^{12}$=H]. To a mixture of 1.09 g (44.7 mmol) of magnesium shavings and 50 mL of THF under nitrogen at ambient temperature was added 15 mL of a solution of 9.44 g (38.8 mmol) of 4-bromoacetophenone ethylene ketal in 100 mL of THF. The resulting mixture was gently heated until a green/yellow coloration was observed (ca. 15 min), at which time the remaining aryl bromide solution was added dropwise over a 10 min period without additional external heating. After 2 h, the resulting olive-green suspension was cooled to between −0° C. and −13° C., and then 851 mg (8.60 mmol) of CuCl was added in one portion, followed 15 sec later by a solution of 2.85 g (8.60 mmol) of 3,3-[1,2-ethanediylbis(oxy)]-5α,10α-(oxido)estr-9(11)-en-17-one (A-2) in 25 mL of THF, followed by rinsing with 5 mL of THF. After 20 min, the resulting clear yellow mixture was quenched with saturated aq $NH_4Cl$ and allowed to warm to ambient temperature. Ether and water were added, and the mixture was extracted with ether. The combined organic solutions were washed with brine, dried over $MgSO_4$, filtered, and the solvent was removed under reduced pressure. The resulting solid was taken up in a minimal amount of $CH_2Cl_2$ and chromatographed on silica gel (hexanes-ether, 1:22 to 100% ether) to afford 1,4-adduct A-3 ($R^1$=4-$CH_3C(OCH_2)_2$—, $R^{12}$=H) (3.45 g, 81% yield) as a $R^{12}$=H), white foamy solid. $^1H$ NMR (250 MHz, $CDCl_3$) δ 7.35, 7.19 (ABq, 4, J=8.3 Hz), 4.39 (s, 1), 4.32 (d, 1, J=7.4 Hz), 4.03–3.77 (m, 8), 1.64 (s, 3), 0.47 (s, 3).

3,3-[1,2-Ethanediylbis(oxy)]-11β-{4-{1,1-[1,2-ethanediylbis(oxy)]ethyl}phenyl}-5α-hydroxyestr-9-en-17-oxime [A-4 ($R^1$=4-$CH_3C(OCH_2)_2$—, $R^{12}$=H)]. To a mixture of 3.45 g (6.97 mmol) of ketone A-3 ($R^1$=4-$CH_3C(OCH_2)_2$—, $R^{12}$=H) and 557 mg (8.02 mmol) of hydroxylamine hydrochloride under nitrogen at ambient temperature was added 25 mL of anhydrous pyridine, then 2.5 h later, 242 mg (3.49 mmol) of additional hydroxylamine hydrochloride was added. After 12 h, the reaction mixture was poured into 250 mL of water and extracted with ether. The combined organic solution was washed with brine, dried over $MgSO_4$, filtered, and the solvent was removed under reduced pressure. The resulting white solid was taken up in a minimal amount of $CH_2Cl_2$ and chromatographed on silica gel (14% $Me_2CO$ in $CH_2Cl_2$) to afford oxime A-4 ($R^1$=4-$CH_3C(OCH_2)_2$—, $R^{12}$=H) (2.97 g, 84% yield) as a white solid foam. $^1H$ NMR (250 MHz, $CDCl_3$) δ 7.34, 7.19 (ABq, 4, J=8.4 Hz), 6.95 (br s, 1), 4.38 (s, 1), 4.30 (d, 1, J=6.8 Hz), 4.05–3.77 (m, 4), 1.64 (s, 3), 0.51 (s, 3).

17-Bromo-3,3-[1,2-ethanediylbis(oxy)]-11β-{4-{1,1-[1,2-ethanediybis(oxy)]-ethyl}phenyl}-5α-hydroxy-17-nitroestr-9ene. To a rapidly stirring mixture of 523 mg (2.94 mmol) of NBS in 1.7 mL of water and 1.7 mL of dioxane at ambient temperature was added a solution of 295 mg (2.94 mmol) of $KHCO_3$ in 1.7 mL of water. To the resulting mixture was added a solution of 500 mg (0.981 mmol) of oxime A-4 ($R^1$=4-$CH_3C(OCH_2)_2$-$R^{12}$=H) in 3.4 mL of dioxane dropwise, followed by rinsing with 0.4 mL of dioxane, causing a light lime-green coloration. After stirring vigorously for 17 h, the resulting off-white mixture was diluted with ether and water, then extracted with ether. The combined organic solutions were washed once with water, three times with 50% saturated aq $FeSO_4$ solution, twice with brine, dried over $MgSO_4$, filtered, and the solvent was removed under reduced pressure. Without excessive delay, the resulting glassy yellow foam was taken up in a minimal amount of $CH_2Cl_2$ and chromatographed on silica gel (50% EtOAc in hexanes) to afford the desired but highly labile 17-bromo-17-nitro compound (437 mg, 74% yield) as a white solid foam. IR ($CCl_4$) n 3500, 1548 $cm^{-1}$]; $^1H$ NMR (250 MHz, $CDCl_3$) δ 7.35, 7.17 (ABq, 4, J=8.3 Hz), 4.43 (s, 1), 4.39 (d, 1, J=7.2 Hz), 4.08–3.75 (m, 8), 3.32 (m, 1), 1.63 (s, 3), 0.45 (s, 3).

3,3-[1,2-Ethanediylbis(oxy)]-11β-{4-{1,1-[1,2-ethanediylbis(oxy)]ethyl}phenyl}-5α-hydroxy-17-nitroestr-9-ene [A-5 ($R^1$=4-$CH_3C(OCH_2)_2$—, $R^{12}$=H)]. To a solution of 200 mg (0.331 mmol) of the 17-nitro-17-bromo alcohol compound described above in 3.4 mL of THF and 0.6 mL of water at ambient temperature was added 39.0 mg (1.03 mmol) of $NaBH_4$ in one portion, ensuing a vigorous exothermic reaction. After 1.4 h, 11.0 mg (0.30 mmol) of additional $NaBH_4$ was added. After 2.6 h, the reaction mixture volume was doubled by the addition of ether, and a solution of 228 mg (3.28 mmol) of hydroxylamine hydrochloride in 6 mL of water was added dropwise over 4 min to the vigorously stirred reaction mixture. After stirring for 5 min, the mixture was extracted with ether. The combined organic solutions were washed with water, saturated aq $NaHCO_3$ solution, and brine, dried over $MgSO_4$, filtered, and the solvent was removed under reduced pressure. The resulting foam was taken up in a minimal amount of $CH_2Cl_2$ and chromatographed on silica gel (50% EtOAc in hexanes) to afford the debrominated nitro alcohol A-5 ($R^1$=4-$CH_3C(OCH_2)_2$—, $R^{12}$H) (152 mg, 87% yield) as a white fluffy solid. $^1H$ NMR (250 MHz, $CDCl_3$) δ 7.34, 7.16 (ABq, 4, J=8.3 Hz), 4.41 (s, 1), 4.38–4.31 (m, 2), 4.02–3.72 (m, 4), 2.74 (d, 1, J=13 Hz), 1.63 (s, 3), 0.32 (s, 3).

17α-(2-Carbomethoxyethyl)-3,3-[1,2-ethanediylbis(oxy)]-11β-{4-{1,1-[1,2-ethanediylbis(oxy)]ethyl}phenyl}-5α-hydroxy-17β-nitroestr-9-ene [A-6($R^1$=4-$CH_3C(OCH_2)_2$—, $R^7$=—$(CH_2)_2COOMe$, $R^{12}$=H)]. To a mixture of 146 mg (0.278 mmol) of nitro alcohol A-5 ($R^1$=4-$CH_3C(OCH_2)_2$—, $R^{12}$=H) in 0.80 mL of t-BuOH and 1.51 mL (16.7 mmol) of methyl acrylate at ambient temperature was added dropwise 0.16 mL (0.35 mmol) of 40% w/w Triton B in methanol, causing a homogeneous faintly yellow reaction solution. After 1 h, ether and saturated aq $NH_4Cl$ solution were added, and the mixture was extracted with ether. The combined organic solution was washed with water then with brine, dried over $MgSO_4$, filtered, and the solvent was removed under reduced pressure. The resulting off-white solid was taken up in a minimal amount of $CH_2Cl_2$ and chromatographed on silica gel (70% EtOAc in hexanes) to afford methyl ester A-6 ($R^1$=4-$CH_3C(OCH_2)_2$—, $R^7$=—$(CH_2)_2COOMe$, $R^{12}$=H) (142 mg, 84% yield) as a white foamy solid. $^1H$ NMR (250 MHz, $CDCl_3$) δ 7.34, 7.16 (ABq, 4, J=8.1 Hz), 4.37 (br s, 2), 4.01–3.74 (m, 4), 3.69 (s, 3), 1.62 (s, 3), 0.33 (s, 3).

3,3-[1,2-Ethanediylbis(oxy)]-11β-{4-{1,1-[1,2-ethanediylbis(oxy)]ethyl}phenyl}-5α-hydroxy-17α-(3-hydroxypropyl)-17β-nitroestr-9-ene [A-7 ($R^1$=$CH_3C(OCH_2)_2$—, $R^7$=—$(CH_2)_3OH$, $R^{12}$=H]. To a solution of 142 mg (0.232 mmol) of ester A-6 ($R^1$=4-$CH_3C(OCH_2)_2$—, $R^7$=—$(CH_2)_2COOMe$, $R^{12}$=H) in 2.3 mL of THF at −78° C. under nitrogen was added dropwise 0.80 mL (0.80 mmol) of 1.0 M DIBAL-H in hexanes. After 1.25 h, saturated aq Rochelle's salt was added and the mixture was allowed to warm to ambient temperature and stir until the resulting emulsion cleared (ca. 1.5 h). Ether and water were added, and the resulting mixture was extracted with ether. The combined organic solution was washed with brine, dried over $MgSO_4$, filtered, and the solvent was removed under reduced pressure to afford a mixture of starting ester A-6 ($R^1$=4-$CH_3C(OCH_2)_2$—, $R^7$=—$(CH_2)_2COOMe$, $R^{12}$=H) and intermediate aldehyde by $^1H$ NMR analysis, as a white oily solid (141 mg).

To the above crude product mixture (141 mg) in 2.3 mL of THF at −78° C. under nitrogen was added dropwise 1.20 mL (1.20 mmol) of 1.0 M DIBAL-H in hexanes. After 45 min, the reaction mixture was warmed to 0° C. for 15 min, then re-cooled to −78° C. and quenched with saturated aq Rochelle's salt, then allowed to warm to ambient temperature and stir. The resulting white mixture was extracted with ether. The combined white organic solutions were washed with brine, saturated aq Rochelle's salt, water, twice with brine, dried over MgSO$_4$, filtered, and the solvent was removed under reduced pressure to afford a white solid (74 mg). After standing for ca. 2 h, the combined aqueous layers had become clear, and were re-extracted with EtOAc. The EtOAc extracts were washed with brine, dried over MgSO$_4$, filtered, and the solvent was removed under reduced pressure to afford a white solid (54 mg). The two crude products were combined in a minimal amount of CH$_2$Cl$_2$ and chromatographed on silica gel (90% EtOAc in hexanes) to afford diol A-7 (R$^1$=4-CH$_3$C(OCH$_2$)$_2$—, R$^7$=—(CH$_2$)$_3$OH, R$^{12}$=H) (98 mg, 73% yield) as a white solid. $^1$H NMR (250 MHz, CDCl$_3$) δ 7.34, 7.16 (ABq, 4, J=8.2 Hz), 4.37 (m, 2), 4.02–3.66 (m, 10), 2.83 (m, 1), 2.60 (d, 1, J=13 Hz), 1.63 (s, 3), 0.33 (s, 3).

11β-(4-Acetylphenyl)-17α-(3-hydroxypropyl)-17β-nitroestra-4,9-dien-3-one [A-8 (R$^1$=4-CH$_3$CO—, R$^7$=—(CH$_2$)$_3$OH, R$^{12}$=H). To a well-stirred mixture of 67.0 mg (0.115 mmol) of the diol A-7 (R$^1$=4-CH$_3$C(OCH$_2$)$_2$-, R$^7$=—(CH$_2$)$_3$OH, R$^{12}$=H), 3.0 mL of CH$_2$Cl$_2$, and 0.05 mL of H$_2$O at 0° C. was added 0.50 mL of TFA dropwise, causing a yellow coloration. After 15 min, saturated aq NaHCO$_3$ was added, the layers were separated, and the aqueous layer was extracted three times with CH$_2$Cl$_2$. The combined organic solution was washed with brine, dried over Na$_2$SO$_4$, filtered, and the solvent was removed under reduced pressure. The crude product was taken up in a minimal amount of CH$_2$Cl$_2$ and chromatographed on silica gel (85% EtOAc in hexanes) to afford A-8 (R$^1$=4-CH$_3$CO—, R$^7$=—(CH$_2$)$_3$OH, R$^{12}$=H) (47.2 mg, 86% yield). $^1$H NMR (500 MHz, CDCl$_3$) δ 7.87, 7.28 (ABq, 4, J=8.3 Hz), 5.80 (s, 1), 4.51 (d, 1, J=7.1 Hz), 3.72 (m, 1), 3.62 (m, 1), 2.86 (t, 1, J=13.4 Hz), 2.72 (m, 2), 2.60 (m, 2), 2.56 (s, 3), 2.55–2.51 (m, 1), 2.46–2.26 (m, 5), 2.09–2.04 (m, 1), 1.96–1.90 (m, 1), 1.84–1.74 (m, 2), 1.70–1.61 (m, 3), 1.53–1.42 (m, 2), 1.21–1.14 (m, 1), 0.39 (s, 3).

EXAMPLE 6

Synthesis of E- and Z-11β-(4-Acetylphenyl)-17α-[1-(3-hydroxy)-propenyl]-17β-nitroestra-4,9-dien-3-one [A-8 (R$^1$=4-CH$_3$CO—, R$^7$=HOCH$_2$CH═CH—, R$^{12}$=H)]

17α-[(E)-2-Carbomethoxyethenly]-3,3-[1,2-ethanediylbis(oxy)]-11β-{4-{1,1-[1,2-ethanediylbis(oxy)]ethyl}phenyl}-5α-hydroxy-17βnitroestr-9-ene [A-6 (R$^1$=4CH$_3$C(OCH$_2$)$_2$, R$^7$=(E) MeOOCCH═CH—, R$^{12}$=H)] and 17α-[(Z)-2-Carbomethoxy-ethenyl]-3,3-[1,2-ethanediylbis(oxy)]-11β-{4-{1,1-[1,2-ethanediylbis(oxy)]ethyl}phenyl}-5α-hydroxy-17β-nitroestr-9-ene [A-6 (R$^1$=4-CH$_3$C(OCH$_2$)$_2$, R$^7$=(Z) MeOOCCH═CH—, R$^{12}$=H)]. To a mixture of 2000 mg (3.80 mmol) of nitro compound A-5 (R$^1$=4-CH$_3$C(OCH$_2$)$_2$—, R$^{12}$=H), 2.45 g (7.61 mmol) of Bu$_4$NBr, 1.10 g (19.0 mmol) of KF, and 10 mL of DMSO in a flame-dried flask under nitrogen at room temperature was added 0.68 mL (7.61 mmol) of methyl propiolate. After 1.5 h, the sides of the flask were rinsed with an additional 3 mL of DMSO. After 2.5 h, EtOAc and H$_2$O were added and the aqueous layer was separated and extracted with EtOAc. The combined organic solution was washed with brine, dried over MgSO$_4$, filtered, and the solvent was removed under reduced pressure. The resulting brown foamy solid was taken up in a minimal amount of CH$_2$Cl$_2$ and chromatographed on silica gel (60% EtOAc in hexanes) to afford a 3:1 mixture of A-6 (R$^1$=4-CH$_3$C(OCH$_2$)$_2$—, R$^7$=(E) MeOOCCH═CH—, R$^{12}$=H) and A-6 (R$^1$=4-CH$_3$C(OCH$_2$)$_2$, R$^7$=(Z) MeOOCCH═CH—, R$^{12}$=H) (2.13 g, 92%). Medium pressure chromatography (MPLC) on silica gel (application with a minimal amount of CH$_2$Cl$_2$, elution with 32:67:1, THF-hexanes-MeOH) afforded pure A-6 (R$^1$=4-CH$_3$C(OCH$_2$)$_2$, R$^7$=(E) MeOOCCH═CH—, R$^{12}$=H) (1.104 g) and two mixtures of A-6 (R$^1$=4-CH$_3$C(OCH$_2$)$_2$, R$^7$=(E) MeOOCCH═CH—, R$^{12}$=H) and A-6 (R$^1$=4-CH$_3$C(OCH$_2$)$_2$, R$^7$=(Z) MeOOCCH═CH—, R$^{12}$=H) (142 mg of ca. 1:1 and 304 mg of 13:87, respectively). Two recrystallizations of the 304 mg, 13:87 mixture from 32:67:1, THF-hexanes-MeOH afforded pure A-6 (R$^1$=4-CH$_3$C(OCH$_2$)$_2$, R$^7$=(Z) MeOOCCH═CH—, R$^{12}$=H) (200 mg). $^1$H NMR (250 MHz, CDCl$_3$) A-6 (R$^1$=4-CH$_3$C(OCH$_2$)$_2$, R$^7$=(E) MeOOCCH═CH—, R$^{12}$=H) δ 7.35, 7.16 (ABq, 4, J=8.2 Hz), 7.36 (d, 1, J=16 Hz), 5.86 (d, 1, J=16 Hz), 4.44 (s, 1), 4.30 (d, 1, J=7.5 Hz), 4.05–3.72 (m, 8), 3.81 (s, 3), 2.95 (m, 1), 2.67 (d, 1, J=13 Hz), 1.63 (s, 3), 0.43 (s, 3); A-6 (R$^1$=4-CH$_3$C(OCH$_2$)$_2$, R$^7$=(Z) MeOOCCH═CH—, R$^{12}$=H) δ 7.33, 7.13 (ABq, 4, J=8.2 Hz), 6.60 (d, 1, J=13 Hz), 5.99 (d, 1, J=13 Hz), 4.44 (s, 1), 4.39 (br s, 1), 4.06–3.68 (m, 8), 3.68 (s, 3), 3.34 (m, 1), 1.62 (s, 3), 0.38 (s, 3).

3,3-[1,2-Ethanediylbis(oxy)]-11β-{4-{1,1-[1,2-ethanediylbis(oxy)]ethyl}phenyl}-5α-hydroxy-17α-[(E)-1-(3-hydroxy)propenyl]-17β-nitroestr-9-ene [A-7 (R$^1$=4-CH$_3$C(OCH$_2$)$_2$—, R$^7$=(E) HOCH$_2$CH═CH—, R$^{12}$=H)]. To a solution of 557 mg (0.914 mmol) of ester A-6 (R$^1$=4-CH$_3$C(OCH$_2$)$_2$, R$^7$=(E) MeOOCCH═CH—, R$^{12}$ =H) in 9.2 mL of THF at −78° C. under nitrogen was added 4.6 mL (4.57 mmol) of 1.0 M DIBAL-H in hexanes dropwise. After 35 min, the solution was warmed to 0° C. for 30 min, then recooled to −78° C. and quenched with saturated Rochelle's salt and allowed to warm to room temperature and stirred for 12 h. The resulting clear mixture was diluted with EtOAc and the aqueous layer was separated and extracted three times with EtOAc. The combined organic solution was washed twice with brine, dried over Na$_2$SO$_4$, filtered, and the solvent was removed under reduced pressure. The resulting white solid was taken up in a minimal amount of CH$_2$Cl$_2$ and chromatographed on silica gel (EtOAc) to afford allyl alcohol A-7 (R$^1$=4-CH$_3$C(OCH$_2$)$_2$, R$^7$=(E) HOCH$_2$CH═CH—, R$^{12}$=H) (464 mg, 87%). $^1$H NMR (250 MHz, CDCl$_3$) δ 7.33,7.16 (ABq, 4, J=8.1 Hz), 6.26 (d, 1, J=16 Hz), 5.80 (dt, 1, J=16, 4.7 Hz), 5.02 (s, 1), 4.47 (m, 2), 4.13–3.75 (8H, m), 2.85 (m, 1), 2.65 (d, 1, J=13 Hz), 1.63 (s, 3), 0.40 (s, 3).

11β-(4-Acetylphenyl)-17α-[(Z)-1-(3-hydroxy)propenyl]-17β-nitroestra-4,9-dien-3-one [A-8 (R$^1$=4-CH$_3$CO—, R$^7$=(Z) HOCH$_2$CH═CH—, R$^{12}$=H)]. To a solution of 200 mg (0.328 mmol) of ester A-6 (R$^1$=4-CH$_3$C(OCH$_2$)$_2$, R$^7$=(E) MeOOCCH═CH—, R$^{12}$=H) in 6.6 mL of THF at −78° C. under nitrogen was added 1.7 mL (1.64 mmol) of 1.0 M DIBAL-H in hexanes dropwise. The solution was then warmed to 0° C. for 30 min, then re-cooled to −78° C. and quenched with saturated aq Rochelle's salt. The resulting mixture was allowed to warm to room temperature and stir for 12 h. The resulting clear mixture was extracted with EtOAc. The combined organic solution was washed twice with brine, dried over Na$_2$SO$_4$, filtered, and the solvent was removed under reduced pressure. Chromatography of the residue on silica gel (EtOAc) afforded allylic alcohol A-7 (R$^1$=4-CH$_3$C(OCH$_2$)$_2$—, R$^7$=(Z) HOCH$_2$CH═CH—, R$^{12}$=H). The product was suspended in 7.8 mL of CH$_2$Cl$_2$ and 0.14 mL of H$_2$O, cooled to 0° C., and 1.3 mL of TFA was added dropwise to the rapidly stirred mixture. After 20 min, saturated aq NaHCO$_3$ solution was added and the mixture was stirred vigorously for 20 min. The aqueous layer was separated and extracted three times with EtOAc. The combined organic solution was washed twice with brine, dried over Na$_2$SO$_4$, filtered, and the solvent was removed under reduced pressure. Twice, the product was taken up in a minimal amount of $CH_2Cl_2$ and chromatographed on silica gel (80% EtOAc in hexanes) to afford dienone alkenol A-8 ($R^1$=4-$CH_3CO$—, $R^7$=(Z) $HOCH_2CH$=$CH$—, $R^{12}$=H) (78 mg, 50% yield, two steps). $^1H$ NMR (250 MHz, $CDCl_3$) δ 7.88, 7.28 (ABq, 4, J=7.5 Hz), 6.00 (d, 1, J=13 Hz), 5.88–5.78 (m, 2), 4.51 (d, 1, J=7.5 Hz), 4.15–4.08 (m, 2), 3.14 (m, 1), 2.58 (s, 3), 0.41 (s, 3).

11β-(4-Acetylphenyl)-17α-[(E)-1-(3-hydroxy)propenyl]-17β-nitroestra-4,9-dien-3-one [A-8 ($R^1$=4-$CH_3CO$—, $R^7$=(E) $HOCH_2CH$=$CH$, $R^{12}$=H)]. To a rapidly stirred mixture of 464 mg (0.798 mmol) of diol A-7 ($R^1$=4-$CH_3C(OCH_2)_2$, $R^7$=(E) $HOCH_2CH$=$CH$—, $R^{12}$=H), 19 mL of $CH_2Cl_2$, and 0.35 mL of $H_2O$ at 0° C. was added dropwise 3.25 mL of TFA, causing a yellow coloration. After 15 min, saturated aq $NaHCO_3$ solution was slowly added, and the resulting mixture was stirred vigorously for 20 min at 0° C., at which time the aqueous layer was separated and extracted three times with EtOAc. The combined organic extract was washed twice with brine, dried over $Na_2SO_4$, filtered, and the solvent was removed under reduced pressure. The resulting yellow solid was taken up in a minimal amount of $CH_2Cl_2$ and chromatographed on silica gel (80% EtOAc in hexanes) to provide target compound A-8 ($R^1$=4-$CH_3CO$—, $R^7$=(E) $HOCH_2CH$=$CH$—, $R^{12}$=H) (313 mg, 82%). $^1H$ NMR (250 MHz, $CDCl_3$) δ 7.88, 7.28 (ABq, 4, J=8.4 Hz), 6.29 (d, 1, J=16 Hz), 5.91–5.80 (m, 2), 4.44 (d, 1, J=7.5 Hz), 4.30 (d, 2, J=3.1 Hz), 2.90 (m, 1), 2.57 (s, 3), 0.47 (s, 3).

EXAMPLE 7

Synthesis of 17α-(3-Hydroxypropyl)-11β-[4-(methylsulfinyl)phenyl]-17β-nitroestra-4,9-dien-3-one [A-8 ($R^1$=4-$CH_3S(O)$—, $R^7$=—$(CH_2)_3OH$, $R^{12}$=H)] and 17α-(3-Hydroxypropyl)-11β-[4-(methylthio)phenyl]-17β-nitroestra-4,9-dien-3-one [A-8 ($R^1$=4-$CH_3S$—, $R^7$=—$(CH_2)_3$ OH, $R^{12}$=H)]

3,3-[1,2-Ethanediylbis(oxy)]-5α-hydroxy-11β-[4-(methylthio)phenyl)]estr-9-en-17-one [A-3 ($R^1$=4-$CH_3S$—, $R^{12}$=H)]. A flask equipped with stirbar, reflux condenser, addition funnel, and a dry nitrogen inlet and outlet was charged with 2.27 g (93.1 mmol) of Mg shavings, then the apparatus was flame-dried under a stream of dry nitrogen. After cooling to room temperature under a stream of dry nitrogen, the remainder of the protocol was performed under a static pressure of dry nitrogen and at room temperature. To the magnesium shavings was added 100 mL of THF, then ca. 10 mL of a solution of 18.2 g (89.5 mmol) of 4-bromothioanisole in 100 mL of THF was added quickly, thus causing Grignard reagent initiation after a few minutes. The remaining 4-bromothioanisole solution was then added dropwise over a 1.5 h period. After 30 min, 3.54 g (35.8 mmol) of CuCl powder was added with efficient stirring, then 45 sec later, a solution of 11.8 g (35.8 mmol) of epoxide A-2 in 100 mL of THF was added rapidly. After 10 min, the reaction mixture was quenched carefully with excess saturated aq $NH_4Cl$ solution at room temperature. The mixture was diluted with water and extracted three times with EtOAc. The combined organic solutions were washed three times with brine, dried over $Na_2SO_4$, filtered, and the solvent was removed under reduced pressure. The resulting brown oily solid (22.6 g) was chromatographed on silica gel (60% EtOAc in hexanes) to afford thioether A-3 ($R^1$=4-$CH_3S$—, $R^{12}$=H) as a white solid (14.0 g, 86% yield). $^1H$ NMR (250 MHz, $CDCl_3$) δ 7.14 (s, 4), 4.38 (s, 1), 4.28 (d, 1, J=7.2 Hz), 4.02–3.90 (m, 4), 2.46 (s, 3), 0.498 (s, 3).

3,3-[1,2-Ethanediylbis(oxy)]-5α-hydroxy-11β-[4-(methylthio)phenyl]estr-9-en-17-oxime [A-4 ($R^1$=4-$CH_3S$—, $R^{12}$=H)]. To a solution of 15.2 g (33.4 mmol) of ketone A-3 ($R^1$=4-$CH_3S$—, $R^{12}$=H) in 120 mL of anhydrous pyridine at room temperature under nitrogen was added 3.83 g (55.2 mmol) of $H_2NOH$•HCl. After 25 h, the solution was poured into 500 mL of water. The mixture was extracted three times with EtOAc. The combined organic solutions were washed three times with brine, dried over $Na_2SO_4$, filtered, and the solvent was removed under reduced pressure. Three sequential times, the residue was diluted with toluene then evaporated under reduced pressure (to remove pyridine). Chromatography on silica gel (70% EtOAc in hexanes) afforded oxime A-4 ($R^1$=4-$CH_3S$—, $R^{12}$=H) (15.3 g, 98% yield) as a white foam. $^1H$ NMR (250 MHz, $CDCl_3$) δ 8.18 (br s, 1), 7.14 (s, 4), 4.38 (s, 1), 4.26 (d, 1, J=6.9 Hz), 4.08–3.89 (m, 4), 2.46 (s, 3), 0.539 (s, 3).

3,3-[1,2-Ethanediylbis(oxy)]-5α-hydroxy-11β-[4-(methylsulfinyl)phenyl]-17-nitroestr-9ene [A-5 ($R^1$=4-$CH_3S(O)$—, $R^{12}$=H). To a solution of 21.0 g (118 mmol) of NBS in 80 mL of 1,4-dioxane and 80 mL of water at room temperature was added a solution of 11.8 g (118 mmol) of $KHCO_3$ in 80 mL of water. After 5 min, a solution of 15.8 g (33.7 mmol) of oxime A-4 ($R^1$=4-$CH_3S$—, $R^{12}$=H) in 120 mL of 1,4-dioxane and 80 mL of water was added over a period of 5 min, causing a bright lime-green coloration, which gradually faded to yellow. After 20 h, freshly prepared saturated aqueous $FeSO_4$ (1000 mL) and EtOAc were added. The mixture was filtered through a pad of Celite 545, which was rinsed with EtOAc. The resulting green aqueous layer was separated and extracted twice with EtOAc. The combined organic solution was washed with freshly prepared saturated aqueous $FeSO_4$ solution, twice with brine, dried over $Na_2SO_4$, filtered, and the solvent was removed under reduced pressure to afford the crude 17-nitro-17-bromo intermediate (21.6 g) as a yellow foam, which was used without further purification. $^1H$ NMR (250 MHz, $CDCl_3$) δ 7.56, 7.40 (Abq, 4, J=8.1 Hz), 4.44 (br s, 2), 4.30–3.93 (m, 4), 3.32 (m, 1), 2.72 (s, 3), 0.454 (s, 3). MS m/z (rel inten) 563 ($M^+$, 3), 561 ($M^+$, 2), 483 (17), 467 (20), 334 (31) 99 (100).

To this crude product in 300 mL of THF and 60 mL of water at room temperature was carefully added 4.33 g (144 mmol) of $NaBH_4$ portionwise over ca. 30 min. After 1.5 h at room temperature, a solution of 24.6 g (353 mmol) of $H_2NOH$•HCl in 500 mL of water was carefully added. After 10 min of vigorous stirring, the mixture was extracted three times with EtOAc. The combined organic solutions were washed twice with brine, dried over $Na_2SO_4$, filtered, and the solvent was removed under reduced pressure to afford nitro intermediate A-5 ($R^1$=4-$CH_3S(O)$—, $R^{12}$=H) [15.8 g, 94% yield (highly pure by TLC analysis)]. In a previous smaller (75 mg) scale procedure, chromatography on silica gel (4% MeOH in EtOAc) afforded 49.2 mg (76% yield) of nitro intermediate A-5 ($R^1$=4-$CH_3S(O)$—, $R^{12}$=H). $^1H$ NMR (250 MHz, $CDCl_3$) δ 7.50 (dd, 2, J=3.0, 8.4 Hz), 7.33 (d, 2, J=8.3 Hz), 4.36–4.31 (m, 3), 3.97–3.87 (m, 4), 2.66 (s, 3), 0.271 (s, 3). MS m/z (rel inten) 501 ($M^+$, 18), 483 (50), 466 (32), 380 (39), 99 (100).

17α-(2-Carbomethoxyethyl)-3,3-[1,2-ethanediylbis(oxy)]-5α-hydroxy-11β-[4-(methylsulfinyl)phenyl]-17β-nitroestr-9-ene [A-6 ($R^1$=4-$CH_3S(O)$—, $R^7$=—$(CH_2)_2COOMe$, $R^{12}$=H)]. To a mixture of 1.00 g (1.99 mmol) of nitro sulfoxide A-5 ($R^1$=4-$CH_3S(O)$—, $R^{12}$=H) in 5.80 mL of t-BuOH and 11.0 mL (122 mmol) of methyl acrylate at room temperature was added dropwise 1.15 mL (2.51 mmol) of 40% w/w Triton B in methanol, causing a homogeneous faintly yellow reaction solution. After 3 h, saturated aq $NH_4Cl$ solution and EtOAc were added, and the mixture was extracted three times with EtOAc. The combined organic solutions were washed twice with brine, dried over $Na_2SO_4$, filtered, and the solvent was removed under reduced pressure. The resulting slightly yellow liquid was azeotroped successively three times with toluene to afford a yellow viscous oil (1.29 g). The oil was used in the next reaction without further purification. $^1$H NMR δ 7.55 (dd, 2, J=3.0, 8.4 Hz), 7.38 (d, 2, J=8.3 Hz), 4.43 (d, 1, J=7.2 Hz), 4.39 (s, 1), 4.03–3.96 (m, 4), 2.69 (s, 3), 2.71 (d, 3, J=1.2 Hz), 0.336 (s, 3, $C_{18}$ H).

3,3-[1,2-Ethanediylbis(oxy)]-5α-hydroxy-17α-(3-hydroxypropyl)-11β-[4-(methylthio)phenyl]-17β-nitroestr-9-ene [A-7 ($R^1$4-$CH_3$S—, $R^7$=—$(CH_2)_3$OH, $R^{12}$=H)] and 3,3-[1,2-Ethanediylbis(oxy)]-5α-hydroxy-17α-(3-hydroxypropyl)-11β-[4-(methylsulfinyl)phenyl)-17βnitroestr-9-ene [A-7 ($R^1$=4-$CH_3$S(O)—, $R^7$=—$(CH_2)_3$OH, $R^{12}$=H). To a solution of 1.29 g (1.99 mmol assumed) of methyl ester A-6 ($R^1$=4-$CH_3$S(O)—, $R^7$=—$(CH_2)_2$COOMe, $R^{12}$=H) in 25.0 mL of THF at −78° C. was added dropwise 12.0 mL (12.0 mmol) of 1.0 M DIBAL-H in hexanes. After 10 min, it was warmed to 0° C. for 1 h at which time TLC analysis showed complete consumption of starting material and the presence of two new compounds. Saturated aq Rochelle's salt and EtOAc were added, and the resulting cloudy mixture was stirred at room temperature for 8 h, thus affording a clear mixture. The aqueous layer was separated and extracted three times with EtOAc. The combined organic solution was washed twice with brine, dried over $Na_2SO_4$, filtered, and the solvent was removed under reduced pressure. Chromatography (2.5% MeOH in EtOAc to 5.0% MeOH in EtOAc) afforded sulfide diol A-7 ($R^1$4-$CH_3$S—, $R^7$=—$(CH_2)_3$OH, $R^{12}$=H) (397 mg, 37% yield for two steps) as a white foam and sulfoxide diol A-7 ($R^1$=4-$CH_3$S(O)—, $R^7$=—$(CH_2)_3$OH, $R^{12}$=H) (310 mg, 28% yield for two steps) as a white foam. $^1$H NMR: Data for sulfide A-7 ($R^1$=4-$CH_3$S—, $R^7$=—$(CH_2)_3$OH, $R^{12}$=H) δ 7.13 (s, 4, ArH), 4.40 (s, 1, $C_5$ OH), 4.32 (d, 1, J=5.0 Hz, $C_{11}$ H), 4.02–3.90 (m, 4, [$OCH_2$]$_2$), 3.58 (m, 2, $CH_2$OH), 2.83 (m, 1), 2.44 (s, 3, $SCH_3$), 0.362 (s, 3, $C_{18}$ H). Data for sulfoxide A-7 ($R^1$=4-$CH_3$S(O)—, $R^7$=—$(CH_2)_3$OH, $R^{12}$=H) δ 7.57 (dd, 2, J=2.2, 8.5 Hz), 7.36 (d, 2, J=8.3 Hz), 5.81 (s, 1), 4.52 (d, 1, J=6.7 Hz), 3.71–3.62 (m, 4), 2.72 (s, 3), 0.395 (s, 3, $C_{18}$ H).

17α-(3-Hydroxypropyl)-11β-[4-(methylthio)phenyl]-17β-nitroestra-4,9-dien-3-one [A-8 ($R^1$=4-$CH_3$S—, $R^7$=—$(CH_2)_3$OH, $R^{12}$=H)]. To a vigorously stirred mixture of 397 mg (0.727 mmol) of sulfide diol A-7 ($R^1$=4-$CH_3$S—, $R^7$=—$(CH_2)_3$OH, $R^{12}$=H), 32.0 mL of $CH_2Cl_2$, and 0.67 mL of water at 0° C. was added 0.89 mL of trifluoroacetic acid. After 3 h, saturated aq $NaHCO_3$ solution was added, and the resulting mixture was stirred at room temperature for 8 h. The mixture was extracted three times with EtOAc. The combined organic solutions were washed with brine, dried over $Na_2SO_4$, filtered, and the solvent was removed under reduced pressure. The residue was chromatographed (75% EtOAc in hexanes). Collection of the fractions determined by analytical HPLC to be >97% pure afforded compound A-8 ($R^1$x4-$CH_3$S—, $R^7$=—$(CH_2)_3$OH, $R^{12}$=H) (186 mg, 53% yield) as a white foam. $^1$NMR δ 7.16 (d, 2, J=8.5 Hz, ArH), 7.08 (d, 2, J=8.5 Hz, ArH), 5.78 (s, 1, vinyl H), 4.43 (d, 1, J=6.5 Hz, $CH_{11}$ H), 3.69–3.59 (m, 2, $CH_2$OH), 2.44 (s, 3, $SCH_3$), 0.427 (s, 3 $C_{18}$ H).

17α-(3-Hydroxypropyl)-11β-[4-(methylsulfinyl)phenyl]-17β-nitroestra-4,9-dien-3-one [A-8 ($R^1$=4-$CH_3$S(O)—, $R^7$=—$(CH_2)_3$OH, $R^{12}$=H)]. To a vigorously stirred mixture of 310 mg (0.552 mmol) of sulfoxide diol A-7 ($R^1$=4-$CH_3$S(O)—, $R^7$=—$(CH_2)_3$OH, $R^{12}$=H), 25.0 mL of $CH_2Cl_2$, and 0.51 mL of water at 0° C. was added 0.67 mL of trifluoroacetic acid. After 3 h, saturated aq $NaHCO_3$ solution was added, and the resulting mixture was stirred at room temperature for 8 h. The mixture was extracted three times with EtOAc. The combined organic solution was washed with brine, dried over $Na_2SO_4$, filtered, and the solvent removed under reduced pressure. The residue was chromatographed (6% MeOH in EtOAc). Collection of the fractions determined by analytical HPLC to be >97% pure afforded compound A-8 ($R^1$-=4-$CH_3$S(O)—, $R^7$=—$(CH_2)_3$OH, $R^{12}$=H) (175 mg, 63% yield) as a white foam. $^1$H NMR δ 7.57, 7.35 (ABq, 4, J=7.7 Hz), 5.81 (s, 1), 4.56 (d, 1, J=6.7 Hz), 3.75–3.55 (m, 2), 2.72 (s, 3), 0.393 (s, 3,$C_{18}$ H).

EXAMPLE 8

Synthesis of 11β-(4-Acetylphenyl)-3',4'-dihydro-5'-methyl-1'-oxo-spiro[estra-4,9-dien-17β,2'(2'H)-pyrrole]-3-one [B-3 ($R^1$=4-$CH_3$CO—, $R^8$=$CH_3$, $R^{12}$=H)]

3,3-[1,2-Ethanediylbis(oxy)]-11β-{4-{1,1-[1,2-ethanediylbis(oxy)]ethyl}phenyl}-5α-hydroxy-17β-nitro-17α-(3-oxobutyl)estr-9-ene [B-1 ($R^1$=4-$CH_3$C($OCH_2$)$_2$—, $R^8$=$CH_3$, $R^{12}$=H)]. To a solution of 2.4 g (4.5 mmol) of A-5 ($R^1$=4-$CH_3$C($OCH_2$)$_2$), $R^{12}$=H) in 10 mL of DMSO was added 1.3 g (22.5 mmol) of KF and 1.45 g (4.5 mmol) of n-$Bu_4$NBr, and the mixture was stirred for 30 min at room temperature. To this mixture was added 0.5 mL (9.0 mmol) of methyl vinyl ketone dropwise and stirring was continued for another hour. The reaction mixture was diluted with water and extracted with ethyl acetate. The organic layer was washed with water, followed by brine, and dried over anhydrous $MgSO_4$. The organic layer was then filtered, concentrated and the crude product chromatographed on silica gel using 5:5:1 methylene chloride-hexane-acetone to give 2.45 g (88% yield) of B-1 ($R^1$=4-$CH_3$C($OCH_2$)$_2$—, $R^8$=$CH_3$, $R^{12}$=H). $^1$H NMR (250 MHz $CDCl_3$) δ 0.33 (s, 3, $C_{18}$ H), 1.64 (s, 3, PhC($OCH_2CH_2$O)$CH_3$), 2.18 (s, 3, $COCH_3$), 3.74–4.01 (m, 8, ($OCH_2$)$_2$), 4.37 (d, 1, $C_{11α}$ H), 4.34 (s, 1, $C_5$ OH), 7.15(d, 2, J=8.1 Hz, ArH), 7.34 (d, 2, J=8.3 Hz, ArH).

3',4'-Dihydro-3,3-[1,2-ethanediylbis(oxy)]-11β-{4-{1,1-[1,2-ethanediylbis(oxy)]-ethyl}phenyl}-5α-hydroxy-5'-methyl-1'oxo-spiro[estr-17β,2'(2'H)-pyrrole]-9-ene [B-2 ($R^1$=4-$CH_3$C($OCH_2$)$_2$—, $R^8$=$CH_3$, $R^{12}$=H)]. To a solution of 1.5 g (2.52 mmol) of B-1 ($R^1$=4-$CH_3$C($OCH_2$)$_2$—, $R^8$=$CH_3$, $R^{12}$=H) in 10 mL of 50% aqueous ethanol and 5.0 mL of THF was added 263 mrg of ammonium chloride and 1.3 g of zinc dust. The reaction mixture was stirred for 24 h, and then filtered through celite. The crude product was chromatographed on silica gel, eluting first with 5:5:1 hexane-methylene chloride-acetone and then with 5:5:1 hexane-methylene chloride-methanol to give 1.13 g (80% yield) of B-2 ($R^1$=4-$CH_3$C($OCH_2$)$_2$—, $R^8$=$CH_3$, $R^{12}$=H). $^1$H NMR (250 MHz $CDCl_3$) δ 0.56 (s, 3, $C_{18}$ H), 1.64 (s, 3, PhC($OCH_2CH_2$O)$CH_3$), 2.21 (s, 3, ON=C—$CH_3$), 3.68–4.02 (m, 8, ($OCH_2$)$_2$), 4.35 (d, 1, $C_{11α}$ H), 5.01 (s, 1, OH), 7.10 (d, 2, J=8.3 Hz, ArH), 7.31 (d, 2, J=8.3 Hz, ArH).

11β-(4-Acetylphenyl)-3',4'-dihydro-5'-methyl-1'-oxo-spiro [estra-4,9-dien-17β,2'(2'H)-pyrrole]-3-one [B-3 ($R^1$=4-$CH_3$CO—, $R^8$=$CH_3$, $R^{12}$=H)]. To a solution of 300 mg of B-2 ($R^1$=4-$CH_3$C($OCH_2$)$_2$—, $R^8$=$CH_3$, $R^{12}$=H) in 5 mL of $CH_2Cl_2$ was added 1.0 mL of trifluroacetic acid (TFA) at 0° C. and the mixture was warmed to room temperature. The reaction was quenched with saturated $NaHCO_3$ solution and extracted with ethyl acetate. The ethyl acetate layer was washed with water followed by brine, and dried over anhydrous $MgSO_4$. The dried solution was filtered and concentrated under vacuum to give 255 mg of crude product which was chromatographed on silica gel using 5:5:1 hexane-methylene chloride-methanol to give 177 mg of pure compound which had the following spectral data: $^1$H NMR (250

MHz CDCl$_3$) δ 0.64 (s, 3, C$_{18}$ H), 2.17 (s, 3, ON=C—CH$_3$), 2.59 (s, 3, PhCOCH$_3$), 4.44 (d, 1, C$_{11\alpha}$ H), 5.81 (s, 1, C$_4$ H), 7.23 (d, 2, J=8.3 Hz, ArH), 7.87 (d, 2, J=8.4 Hz, ArH). MS m/z 457 (M$^+$), 441, 371, 324, 204, 96, 83.

EXAMPLE 9

Synthesis of Synthesis of 3',4'-Dihydro-11β-[4-(N,N-dimethylamino) phenyl]-5'-methyl-1'-oxo-spiro[estra-4,9-dien-17β,2'(2'H)-pyrrole]-3-one [B-3 (R$^1$=4-Me$_2$N—, R$^8$=CH$_3$, R$^{12}$=H)]

11β-[3-Bromo-4-(N,N-dimethylamino)phenyl]-17α-(3-oxobutyl)-3,3-[1,2-ethanediylbis(oxy)]-5α-hydroxy-17β-nitroestr-9-ene [B-1 (R$^1$=4-Me$_2$N—, R$^8$=CH$_3$, R$^{12}$=3-Br). To a solution of 1.51 g (2.69 mmol) of A-5 (R$^1$=4-Me$_2$N—, R$^{12}$=3-Br) in 5 mL of DMSO was added 785 mg (13.45 mmol) of KF and 876 mg (2.69 mmol) of n-Bu$_4$NBr, and the mixture stirred for 30 min. To this mixture was added 0.27 mL (5.38 mmol) of methyl vinyl ketone dropwise, and the solution was stirred for one hour. The reaction mixture was diluted with water and extracted with ethyl acetate. The organic layer was washed with water, followed by brine, and dried over anhydrous MgSO$_4$. The organic layer was filtered, concentrated and the crude product chromatographed on silica gel using 5:5:1 methylene chloride-hexane-acetone to give 1.49 g (88% yield) of B-1 (R$^1$=4-Me$_2$N—, R$^8$=CH$_3$, R$^{12}$=3-Br). I. R. (solution, CDCl$_3$) 3485, 2935, 2775, 1707, 1528, 1481, 1437, 1349, 1131, 965, 935, 826 cm$^{-1}$; $^1$H NMR (250 MHz CDCl$_3$) δ 0.39 (s, 3, C$_{18}$ H), 2.14 (s, 3, COCH$_3$), 2.75 (s, 6, N(CH$_3$)$_2$), 3.91–4.06 (m, 4, (OCH$_2$)$_2$), 4.33 (d, 1, C$_{11\alpha}$ H), 4.39 (s, 1, C$_5$ OH), 6.95 (d, 1, J=8.4 Hz, ArH), 7.09 (d, 1, J=8.5 Hz, ArH), 7.36 (s, 1, ArH).

11β-[3-Bromo-4-(N,N-dimethylamino)phenyl]-3',4'-dihydro-3,3-[1,2-ethanediylbis-(oxy)]-5α-hydroxy-5'-methyl-1'-oxo-spiro[estr-9-ene-17β,2'(2'H)-pyrrole] [B-2 (R$^1$=4-Me$_2$N—, R$^8$=CH$_3$, R$^{12}$=3-Br)]. A solution of the ketone B-1 (R$^1$=Me$_2$N—, R$^8$=CH$_3$, R$^{12}$=3-Br) (1.1 g, 1.599 mmol) was prepared in 5.0 mL of 50% aqueous ethanol and 2.5 mL of THF. To this solution was added 65 mg (1.2 mmol) of NH$_4$Cl and 325 mg (4.9 mmol) of zinc dust. The reaction mixture was stirred overnight and another 325 mg of Zn and 65 mg of ammonium chloride was added and stirring was continued for 8 h. The reaction mixture was filtered through celite and the filtrate concentrated. The crude product was chromatographed on silica gel eluting with 7:3:0.3 methylene cloride-hexane-methanol to give 600 mg (61% yield) of pure B-2 (R$^1$=Me$_2$N—, R$^8$=CH$_3$, R$^{12}$=3-Br). I. R. (solution, CDCl$_3$); 3490, 2936, 2775, 1588, 1481, 1447, 1382, 1214, 966, 887 cm$^{-1}$; $^1$H NMR (250 MHz CDCl$_3$) δ 7.34 (s, 1, ArH), 7.00 (d, 1, J=8.0 Hz, 6.95 (d, 1, J=8.5 Hz, ArH), 4.39 (s, 1, C$_5$ OH), 4.21 (br d, 1, C$_{11\alpha}$ H), 3.93–4.02 (m, 4, (OCH$_2$)$_2$), 2.74 (s, 6, N(CH$_3$)$_2$), 2.14 (s, 3, ON=C—CH$_3$), 0.61 (s, 3, C$_{18}$ H).

3',4'-Dihydro-11β-[4-(N,N-dimethylamino)phenyl]-3,3-[1,2-ethanediylbis(oxy)]-5α-hydroxy-5'-methyl-1'-oxo-spiro[estr-9-ene-17β,2'(2'H)-pyrrole] [B-2 (R$^1$=4-Me$_2$N—, R$^8$=CH$_3$, R$^{12}$=H)]. The aryl bromide B-2 (R$^1$=Me$_2$N—, R$^8$=CH$_3$, R$^{12}$=3-Br) (466 mg, 0.77 mmol) was dissolved in 50 mL of THF and maintained at −78° C. under argon. To this was added 1.9 mL of t-BuLi (1.7 M in pentane) dropwise. After complete addition, the reaction was stirred for 10 min and quenched at −78° C. with methanol (5 mL), followed by saturated NH$_4$Cl solution. The reaction mixture was extracted with ethyl acetate, the organic layer washed with brine and dried over anhydrous MgSO$_4$. The dried solution was filtered and concentrated to give 398 mg of B-2 (R$^1$=Me$_2$N—, R$^8$=CH$_3$, R$^{12}$=H) which was used in the next step without further purification. I. R. (solution, CDCl$_3$) 3490, 2950, 2800, 1608, 1516, 1436, 1345, 1216, 943, 840 cm$^{-1}$; $^1$H NMR (250 MHz CDCl$_3$) δ 7.00 (d, 2, J=8.7 Hz, ArH), 6.62 (d, 2, J=8.7 Hz, ArH), 4.39 (s, 1, C$_5$ OH), 4.21 (d, 1, J=5.9 Hz, C$_{11\alpha}$ H), 3.90–4.02 (m, 4, (OCH$_2$)$_2$), 2.89 (s, 6, N (CH$_3$)$_2$), 2.13 (s, 3, ON=C—CH$_3$), 0.61 (s, 3, C$_{18}$ H).

3',4'-Dihydro-11β-[4-(N,N-dimethylamino)phenyl]-5'-methyl-1'-oxo-spiro[estra-4,9-dien-17β,2'(2'H)-pyrrole])-3-one [B-3 (R$^1$=4-Me$_2$N—, R$^8$=CH$_3$, R$^{12}$=H). To a solution of 398 mg (0.76 mmol) of B-2 (R$^1$=Me$_2$N—, R$^8$=CH$_3$, R$^{12}$=H) in 40 mL of CH$_2$Cl$_2$ was added 2 mL of water. The solution was cooled to 0° C. To the cooled solution was added about 4 mL of TFA dropwise. The reaction was stirred at 0° C. for 1 h. The reaction was quenched with saturated sodium bicarbonate solution, and extracted with CH$_2$Cl$_2$. The CH$_2$Cl$_2$ layer was washed with water, followed by brine and dried over anhydrous MgSO$_4$. The dried solution was filtered and concentrated under vacuum. The crude product was chromatographed on silica gel using 7:3:0.3 methylene chloride-hexane-methanol as eluant to give 251 mg of pure B-3 (R$^1$=Me$_2$N—, R$^8$=CH$_3$, R$^{12}$=H). Further purification was achieved on preparative HPLC on a C-18 reverse phase column using 50% acetonitrile and water: $^1$H NMR (250 MHz CDCl$_3$) δ 7.03 (d, 2, J=8.7 Hz, ArH), 6.81 (d, 2, J=8.7 Hz, ArH), 5.78 (s, 1, C$_4$ H), 4.33 (d, 1, J=6.4 Hz, C$_{11\alpha}$ H), 2.94 (s, 6, N(CH$_3$)$_2$, 2.13 (s, 3, ON=C—CH$_3$), 0.66 (s, 3, C$_{18}$ H); mass spectrum, m/z (rel intensity) 458 (19), 442 (28), 134 (100), 121 (40), 96 (11); Anal. Calcd for C$_{30}$H$_{38}$N$_2$O$_2$•0.25 H$_2$O: C, 77.80; H, 8.38; N, 6.05. Found: C, 77.90; H, 8.89; N, 5.51.

EXAMPLE 10

Synthesis of 11β-[4-(N,N-Dimethylamino)phenyl]-17β-nitro-17α-(1-propynyl)estra-4,9-dien-3-one [(C-2 (R$^1$=4-Me$_2$N—, R$^9$=CH$_3$, R$^{12}$=H)].

11β-[4-(N,N-Dimethylamino)phenyl]-3,3-[1,2-ethanediylbis(oxy)]-5α-hydroxy-17β-nitro-17α-(1-propynyl)estr-9-ene [C-1 (R$^1$=4-Me$_2$N—, R$^9$=CH$_3$, R$^{12}$=H)] and 3,3-[1,2Ethanediylbis(oxy)]-5α-hydroxy-11β-[4-(N-methylamino)phenyl]-17β-nitro-17α-(1-propynyl)estr-9-ene [C-1 (R$^1$=4-MeHN—, R$^9$=CH$_3$, R$^{12}$=H)]. To a solution of 2.39 g (4.94 mmol) of nitro compound A-5 (R$^1$=4-Me$_2$N—, R$^{12}$=H) in 50 mL of DMSO under nitrogen at room temperature was added 312 mg (12.4 mmol) of NaH. After 3.5 h, a solution of 4.89 g (14.8 mmol) of tributyl(1-propynyl)tin (prepared by analogy to Pinhey, J. T.; Maloney, M. G.; Roche, E. G. "The α-Alk-1-ynylation of β-Dicarbonyl Compounds and Nitronate Salts by Alk-1-ynyl-lead Triacetates," *J. Chem. Soc. Perkin Trans.* 1, 333 (1989)) in 7.0 mL of DMSO was added rapidly to a solution of 6.59 g (14.8 mmol) of 99.99% Pb(OAc)$_4$ [ProChem Chemical Co.; prior to its use it was stirred in vacuo at room temperature for 3 h and strictly handled under nitrogen (to remove all traces of acetic acid)] in 35 mL of DMSO at room temperature. After 30 sec, the above dark nitronate solution was added to the resulting Sn-Pb mixture rapidly, causing mild warming. After 40 min, EtOAc and 400 mL of a 1:1, saturated aqueous NH$_4$Cl solution was added. After stirring vigorously, the aqueous layer was separated and extracted three times with EtOAc. The combined organic solutions were shaken with aqueous KF, filtered, separated, washed twice with brine, dried over Na$_2$SO$_4$, filtered, and the solvent was mostly removed under reduced pressure, affording a brown slightly viscous oil. Chromatography of the oil without excessive delay (50% EtOAc in hexanes) afforded propyne C-1 (R$^1$=4-Me$_2$N—, R$^9$=CH$_3$, R$^{12}$=H) (646 mg, 25% yield) as a yellow foam. $^1$H NMR (250 MHz, CDCl$_3$) δ 7.03, 6.62 (ABq, 4, J=8.8 Hz), 4.49 (s, 1), 4.29 (br s, 1), 4.03–3.93 (m, 4), 2.90 (s, 6), 2.89 (m, 1), 1.93 (s, 3), 0.369

(s, 3). Further elution of the column gave the mono-N-methylated derivative [C-1 ($R^1$=4-MeHN—, $R^9$=$CH_3$, $R^{12}$=H)] (497 mg, 20% yield). $^1$H NMR (250 MHz, CDCl$_3$) δ 6.99, 6.50 (ABq, 4, J=8.6 Hz), 4.49 (br s, 1), 4.28 (br s, 1), 4.02 (m, 4), 3.65 (br, s, 1), 2.89 (m, 1), 2.78 (s, 3), 1.92 (s, 3), 0.377 (s, 3).

11β-[4-(N,N-Dimethylamino)phenyl]-17β-nitro-17α-(1-propynyl)estra-4,9-dien-3-one [(C-2 ($R^1$=4-Me$_2$N—, $R^9$=$CH_3$, $R^{12}$=H)]. To a vigorously stirred mixture of 300 mg (0.576 mmol) of C-1 ($R^1$=4-Me$_2$N—, $R^9$=$CH_3$, $R^{12}$=H), 9.3 mL of CH$_2$Cl$_2$ and 0.52 mL of water at 0° C. was added 0.78 mL (10. 1 mmol) of trifluoroacetic acid dropwise. After 45 min of vigorous stirring at 0° C., saturated aqueous NaHCO$_3$ solution was carefully added, and the mixture was stirred at room temperature for 2 h. The aqueous layer was separated and extracted three times with EtOAc. The combined organic solutions were washed twice with brine, dried over Na$_2$SO$_4$, filtered and the solvent was removed under reduced pressure. Chromatography of the residue on silica gel (45% EtOAc in hexanes) afforded >97% pure (HPLC analysis) compound C-2 ($R^1$=4-Me$_2$N—, $R^9$=$CH_3$, $R^{12}$=H) (178.5 mg, 68% yield). Compound C-2 ($R^1$=4-Me$_2$N—, $R^9$=$CH_3$, $R^{12}$=H) of slightly less than 97% purity was obtained from later column fractions (26.4 mg, 10% yield). $^1$H NMR (250 MHz, CDCl$_3$) δ 7.00, 6.64 (ABq, 4, J=8.6 Hz), 5.77 (s, 1), 4.40 (d, 1, J=6.0 Hz), 2.90 (s, 6), 1.94 (s, 3), 0.442 (s, 3). MS m/z (rel inten) 458 (M$^+$, 53), 413 (14), 263 (25), 134 (55), 121 (100). Anal. Calcd. for C$_{29}$H$_{34}$N$_2$O$_3$•0.25 H$_2$O: C, 75.21; H, 7.51; N, 6.05. Found: C, 75.17; H, 7.49; N, 5.98.

EXAMPLE 11

Synthesis of 11β-(4-Acetylphenyl)-17α-ethynyl-17β-nitroestra-4,9-dien-3-one [(C-2 ($R^1$=4-CH$_3$CO—, $R^9$=$R^{12}$=H)].

3,3-[1,2-Ethanediylbis(oxy)]-11β-{4-{1,1-[1,2-ethanediylbis(oxy)ethyl}phenyl}-5α-hydroxy-17α-ethynyl-17β-nitroestr-9-ene [C-1 ($R^1$=4-CH$_3$C(OCH$_2$)$_2$—, $R^9$=$R^{12}$=H)]. To a solution of 1000 mg (1.90 mmol) of nitro compound A-5 ($R^1$=4-CH$_3$C(OCH$_2$)$_2$—, $R^{12}$=H) in 20 mL of DMSO at room temperature under nitrogen was added 101 mg (4.00 mmol) of NaH in one portion, causing gas evolution and an opaque brown coloration. After 1.2 h, a solution of 1.68 mL (5.70 mmol) of tributyl(ethynyl)tin (Aldrich Chemical Co.) in 8 mL of DMSO was added rapidly to a solution of 2.53 g (5.70 mmol) of 99.99% Pb(OAc)$_4$ [ProChem Chemical Co.; prior to use it was successively mixed three times with dry toluene, evaporated under reduced pressure, and back-filled with nitrogen (to remove all traces of acetic acid)] in 10 mL of DMSO under nitrogen at room temperature. After 30 seconds, the above dark nitronate solution was added to the resulting Sn-Pb mixture rapidly, causing mild warming. After 22 h, 200 mL of a 1:1, saturated aq NH$_4$Cl solution was added, followed by the addition of EtOAc. After stirring vigorously, the aqueous layer was separated and extracted three times with EtOAc. The combined brown organic solution was washed twice with brine, dried over MgSO$_4$, filtered, and the solvent was removed under reduced pressure to afford a brown oil. The crude product was chromatographed without delay on silica gel (55% EtOAc in hexanes) to afford ethynyl product C-1 ($R^1$=4-CH$_3$C(OCH$_2$)$_2$—, $R^9$=R]2=H) (586 mg, 56% yield). $^1$H NMR (250 MHz, CDCl$_3$) δ 7.34, 7.16 (ABq, 4, J=8.1 Hz), 4.45 (s, 1), 4.38 (d, 1, J=4.4 Hz), 4.11–3.77 (m, 8), 3.05 (m, 1), 2.79 (s, 1), 1.62 (s, 3), 0.34 (s, 3).

11β-(4-Acetylphenyl)-17α-ethynyl-17β-nitroestra-4,9-dien-3-one [C-2 ($R^1$=4-CH$_3$CO—, $R^9$=$R^{12}$=H)]. To a rapidly stirred mixture of 75.0 mg (0.136 mmol) of alcohol C-1 ($R^1$=4-CH$_3$C(OCH$_2$)$_2$—, $R^9$=$R^{12}$=H), 3.6 mL of CH$_2$Cl$_2$, and 0.06 mL of H$_2$O at 0° C. was added dropwise 0.58 mL of TFA, causing a bright yellow coloration. After 20 min, saturated aq NaHCO$_3$ solution was added and the aqueous layer was separated and extracted three times with EtOAc. The combined organic solution was washed with brine, dried over MgSO$_4$, filtered, and the solvent was removed under reduced pressure. The residue was chromatographed on silica gel (50% EtOAc in hexanes) to afford C-2 ($R^1$=4-CH$_3$CO—, $R^9$=$R^{12}$=H) (38.3 mg, 64% yield). $^1$H NMR (500 MHz, CDCl$_3$) δ 7.88, 7.28 (ABq, 4, J=8.4 Hz), 5.82 (s, 1), 4.53 (s, 1), 3.06 (dt, 1, J=3.0, 12 Hz), 2.84 (s, 1), 2.57 (s, 3), 0.41 (s, 3).

EXAMPLE 12

Synthesis of 11β-(4-Acetylphenyl)-17β-nitro-17α-(1-propynyl)estra-4,9-dien-3-one [(C-2 ($R^1$=4-CH$_3$CO—, $R^8$=$CH_3$, $R^{12}$=H)].

3,3-[1,2-Ethanediylbis(oxy)]-11β-{4-{1,1-[1,2-ethanediylbis(oxy)]ethyl}phenyl}-5α-hydroxy-17β-nitro-17α-(1-propynyl)-estr-9-ene [C-1 ($R^1$=4-CH$_3$C(OCH$_2$)$_2$—, $R^9$=$CH_3$, $R^{12}$=H)]. To a solution of 1000 mg (assumed 1.90 mmol) of impure nitro compound A-5 ($R^1$=4-CH$_3$C(OCH$_2$)$_2$—, $R^{12}$=H) in 20 mL of DMSO at room temperature under nitrogen was added 101 mg (4.00 mmol) of NaH in one portion, causing gas evolution and a dark black/green coloration. After 1.6 h, a solution of 1.88 mL (5.70 mmol) of tributyl(1-propynyl)tin (prepared by analogy to Pinhey, et. al., 1989) in 6 mL of DMSO was added rapidly to a solution of 2.53 g (5.70 mmol) of 99.99% Pb(OAc)$_4$ [ProChem Chemical Co.; prior to use it was successively mixed three times with dry toluene, evaporated under reduced pressure, and back-filled with nitrogen (to remove all traces of acetic acid)] in 14 mL of DMSO under nitrogen at room temperature. After 35 seconds, the above dark nitronate solution was added to the resulting Sn-Pb mixture rapidly, causing mild warming. After 24 h, 200 mL of a 1:1, saturated aq NH$_4$Cl solution was added, followed by the addition of EtOAc. After stirring vigorously, the aqueous layer was separated and extracted three times with EtOAc. The combined brown organic solution was washed twice with brine, dried over MgSO$_4$, filtered, and the solvent was removed under reduced pressure to afford a brown oil. The crude product was chromatographed without delay on silica gel (55% EtOAc in hexanes), then chromatographed a second time on silica gel (55% EtOAc in hexanes) to afford 1-propynyl product C-1 ($R^1$=4-CH$_3$C(OCH$_2$)$_2$—, $R^9$=$CH_3$, $R^{12}$=H) (161 mg, 15% yield). $^1$H NMR (250 MHz, CDCl$_3$) δ 7.33. 7.16 (ABq, 4, J=8.2 Hz), 4.50 (s, 1), 4.38 (br s, 1), 4.10–3.74 (m, 8), 2.98 (m, 1), 1.93 (s, 3), 0.32 (s, 3).

11β-(4-Acetylphenyl)-17β-nitro-17α-(1-propynyl)estra-4,9-dien-3-one [C-2 ($R^1$=4-CH$_3$CO—, $R^9$=$CH_3$, $R^{12}$=H)]. To a well-stirred mixture of 161 mg (0.286 mmol) of C-1 ($R^1$=4-CH$_3$C(OCH$_2$)$_2$—, $R^9$=$CH_3$, $R^{12}$=H), 7.6 mL of CH$_2$Cl$_2$, and 0.13 mL of H$_2$O at 0° C. was added dropwise 0.5 mL of TFA causing a slight darkening of the reaction mixture. After 1 h, saturated aq NaHCO$_3$ solution was added with vigorous stirring. Water and EtOAc were added and the aqueous layer was separated and extracted three times with EtOAc. The combined organic solution was washed three times with saturated aq NaHCO$_3$ solution, twice with brine, dried over MgSO$_4$, filtered, and the solvent was removed under reduced pressure. Chromatography of the residue on silica gel (53% EtOAc in hexanes) gave target compound C-2 ($R^1$=4-CH$_3$CO—, $R^9$=$CH_3$, $R^{12}$=H) (104 mg, 79% yield). $^1$H NMR (250 MHz, CDCl$_3$) δ 7.88, 7.29 (ABq, 4, J=8.4 Hz), 5.82 (s, 1), 4.52 (br s, 1), 2.97 (m, 1), 2.57 (s, 3), 1.95 (s, 3), 0.38 (s, 3).

EXAMPLE 13

Synthesis of 11β-[4-(N,N-Dimethylamino)phenyl]-3',4'-dihydro-1'-oxo-spiro[estra-4,9-dien-17β,2'(2'H)-pyrrole]-3-one [B-3 ($R^1$=4-$Me_2N$—, $R^8$=$R^{12}$=H)].

11β-[4-(N,N-Dimethylamino)phenyl]-3,3-[1,2-ethanediylbis(oxy)]-5α-hydroxy-17α-(propan-3-al)-17β-nitroestr-9-ene [B-1($R^1$=$Me_2N$—, $R^8$=$R^{12}$=H)]. To 0.500 g (0.883 mmol) of the ester A-5 ($R^1$=4-$Me_2N$—, $R^7$=($CH_2$)$_2$COOMe, $R^{12}$=H) dissolved in 2.0 mL of toluene and maintained under an atmosphere of nitrogen at –78° C. was added 0.97 mL of a 1 M solution of DIBAL-H in hexane dropwise. After 1 h another 1.7 mL of DIBAL-H was added and the mixture was stirred at –78° C. for 30 min. The reaction was quenched by adding 0.24 mL of methanol in 0.4 mL of toluene followed by addition of 0.13 mL of water in 0.22 mL of methanol. The reaction mixture was stirred for 30 min and then filtered through celite. The filtrate was concentrated and the crude aldehyde was chromatographed on silica gel using 1.5:1 EtOAc-hexane to give 456 mg of pure B-1 ($R^1$=$Me_2N$—, $R^8$=$R^{12}$=H) in 96% yield. $^1$H NMR (250 MHz, $CDCl_3$) δ 8.76 (s, 1, CHO), 7.04 (d, 2, J=8.7 Hz, 6.63 (d, 2, J=8.7 Hz, ArH), 4.35 (s, 1, $C_5$ OH), 4.28 (d, 1, J=6.6 Hz, $C_{11α}$ H), 3.95 (m, 4, O($CH_2$)$_2$), 3.93–4,02 (m, 2, $CH_2$OH), 2.90 (s, 6, N($CH_3$)$_2$), 0.40 (s, 3, $C_{18}$ H), ArH).

3',4'-Dihydro-11β-[4-(N,N-dimethylamino)phenyl]-3,3-[1,2-ethanebis(oxy)]-5α-hydroxy-1'-oxo-spiro[estr-9-ene17β,2'(2'H)-pyrrole] [B-2 ($R^1$=4-$Me_2N$—, $R^8$=$R^{12}$=H)]. A solution of the aldehyde B-1 ($R^1$=$Me_2N$—, $R^8$=$R^{12}$=H) (0.400 g, 0.74 mmol) was prepared in 4.0 mL of 50% aqueous ethanol and 2.0 mL of THF. To this was added 64 mg (1.19 mmol) of ammonium chloride and 304 mg (4.65 mmol) of zinc dust. The reaction mixture was stirred overnight and another 304 mg of Zn and 64 mg of ammonium chloride was added and stirring was continued for 24 h. The reaction mixture was filtered through celite and the filtrate concentrated. The crude product was chromatographed on silica gel eluting with 5:5:1 methylene chloride-hexane-methanol to give 293 mg (78% yield) of pure B-2 ($R^1$=4-$Me_2N$—, $R^8$=$R^{12}$=H); $^1$H NMR (250 MHz $CDCl_3$) δ 7.00 (d, 1, J=8.4 Hz, ArH), 6,98 (s, 1, ON═CH), 6.62 (d, 2, J=8.8 Hz, ArH), 4.40 (s, 1, $C_5$ OH), 4.21 (d, 1, J=6.4 Hz, $C_{11α\ H}$), 3.93–4.02 (m, 4, (O$CH_2$)$_2$), 2.88 (s, 6, N($CH_3$)$_2$), 0.62 (s, 3, $C_{18}$ H).

3',4'-Dihydro-11β-([4-(N,N-dimethylamino)phenyl]-1'-oxo-spiro[estr-4,9-dien-17β,2'(2'H)-pyrrole]-3-one [B-3 ($R^1$=4-$Me_2N$—, $R^8$=$R^{12}$=H)]. To a solution of 120 mg (0.23 mmol) of 2 ($R^1$=4-$Me_2N$—, $R^8$=$R^{12}$=H) in 2.5 mL of $CH_2Cl_2$ was added 0.1 mL of water and the mixture was cooled to 0° C. To the cooled solution was added about 0.5 mL of TFA dropwise. The reaction was stirred at 0° C. for 1 h. The reaction was then quenched with saturated sodium bicarbonate solution, and extracted with $CH_2Cl_2$. The $CH_2Cl_2$ layer was washed with water, followed by brine and dried over anhydrous $MgSO_4$. The dried solution was filtered and concentrated under vacuum. The crude product was chromatographed on silica gel using 5:5:1 methylene cloride-hexane-methanol as eluant to give 79 mg (76% yield) of pure B-3 ($R_1$=4-$Me_2N$—, $R^8$=$R^{12}$=H). $^1$H NMR (250 MHz $CDCl_3$) δ 7.00 (s, 1, ON═CH), 6.96 (d, 2, J=8.4 Hz, ArH), 6.63 (d, 2, J=8.9 Hz, ArH), 5.77 (s, 1, $C_4$ H), 4.34 (d, 1, J=6.8 Hz, $C_{11α}$ H), 2.90 (s, 6, N($CH_3$)$_2$), 0.70 (s, 3, $C_{18}$ H); mass spectrum, m/z (rel intensity) 444 (43), 428 (62), 278 (12), 134 (86), 121 (100), 91 (12); Anal. Calcd for $C_{29}H_{36}N_2O_2$•1.25 $H_2O$: C, 74.40; H, 8.50; N, 5.98. Found: C, 74.56; H, 8.50; N, 5.43.

EXAMPLE 14

Synthesis of 3',4'-Dihydro-5'-methyl-1'-oxo-11β-[4-(N,N-piperidino) phenyl-spiro[estra-4,9-dien-17β,2'(2'H)-pyrrole]-one [B-3 ($R^1$=4-(N-piperidino), $R^8$=$R^{12}$=H)].

11β-[4-(N-piperidino)phenyl]-3,3-[1,2-ethanediylbis(oxy)]-5α-hydroxy-17β-nitro-17α-(3-oxobutyl)-estr-9-ene [B-1 ($R^1$=4-(N-piperidino)-, $R^8$=$CH_3$ $R^{12}$=H)]. A solution of 0.750 g (1.44 mmol)of A-5 ($R^1$=4-(N-piperidino)-, $R^{12}$=H) 416 mg (7.175 mmol) of KF and 462 mg (1.43 mmol) of n-$Bu_4$NBr in 3.5 mL of DMSO was stirred for 30 min at room temperature. Then 0.14 mL (2.87 mmol) of methyl vinyl ketone was added dropwise and the mixture was stirred for 1 h. The reaction mixture was diluted with water and extracted with ethyl acetate. The organic layer was washed with water, followed by brine and dried over anhydrous $MgSO_4$. The organic layer was then filtered, concentrated and the crude product chromatographed on silica gel using 1:1 hexane-ethyl acetate to give 0.74 g (87% yield) of B-1 ($R^1$=4-(N-piperidino)-, $R^8$=$CH_3$, $R^{12}$=H). $^1$H NMR (250 MHz $CDCl_3$) δ 7.04 (d, 2, J=8.5 Hz, ArH), 6.81 (d, 2, J=8.7 Hz, ArH), 4.32 (s, 1, $C_5$ OH), 4.32 (br d, 1, $C_{11α}$ H), 3.93–4.00 (m, 4, (O$CH_2$)$_2$), 3.09 (t, 4, N($CH_2$)$_2$), 2.17 (s, 3, CO$CH_3$), 0.37 (s, 3, $C_{18}$ H).

3',4'-Dihydro-3,3-[1,2-ethanediylbis(oxy)]-5α-hydroxy-5'-methyl-1'-oxo-11β-[4-(N-piperdino)phenyl]-spiro[estr-9-ene-17β,2'(2'H)-pyrrole] [B-2 ($R^1$=4-(N-piperidino-, $R^8$=$CH_3$, $R^{12}$=H)]. A solution of the ketone B-1 ($R^1$=4-(N-piperidino)-, $R^8$=$CH_3$, $R^{12}$=H) (0.740 g, 1.25 mmol) was prepared in 5.0 mL of 50% aqueous ethanol and 2.5 mL of THF. To this solution was added 56 mg (1.04 mmol) of ammonium chloride and 283 mg (4.42 mmol) of zinc dust. The reaction mixture was stirred overnight and another 283 mg of Zn and 56 mg of ammonium chloride was added and stirring was continued for 8 h. The reaction mixture was filtered through celite and the filtrate concentrated. The crude product was chromatographed on silica gel eluting with 5:1 EtOAc-MeOH to give 670 mg (96% yield) of pure B-2 ($R^1$=4-(N-piperidino)-, $R^8$=$CH_3$, $R^{12}$=H). $^1$H NMR (250 MHz $CDCl_3$) δ 6.99 (d, 2, J=8.6 Hz, ArH), 6.81 (d, 2, J=8.6 Hz, ArH), 4.39 (s, 1, $C_5$ OH), 4.18 (d, 1, J=7.8 Hz, $C_{11α}$ H), 3.93–4.02 (m, 4, (O$CH_2$)$_2$), 3.08 (br t, 4, N($CH_2$)$_2$), 2.05 (s, 3, ON═C—$CH_3$), 0.60 (s, 3, $C_{18}$ H).

3',4'-Dihydro-5'-methyl-1'-oxo-11β-[4-(N-piperidino)phenyl)]-spiro[estr-4,9-dien-17β,2'(2'H)-pyrrole]-3-one [B-3 ($R^1$=4-(N-piperidino)-, $R^8$=$CH_3$, $R^{12}$=H). The ketal B-2 ($R^1$=4-(N-piperidino)-, $R^8$=$CH_3$, $R^{12}$=H) (3.87 g, 6.9 mmol) was dissolved in 25 mL of $CH_2Cl_2$. To this was added 1.0 mL of water and the mixture was cooled to 0° C. To the solution was added about 5.0 mL of TFA dropwise. The reaction was stirred at 0° C. for 1 h during which time it turned from a brownish pink to pale yellow. The reaction was quenched after stirring for another 30 min with saturated sodium bicarbonate solution, and extracted with $CH_2Cl_2$. The organic layer was washed with water, followed by brine and dried over anhydrous $Na_2SO_4$. The dried solution was filtered and concentrated under vacuum. The crude product was chromatographed on silica gel using 5:1 EtOAc-MeOH as eluant to give 1.67 g of pure B-3 ($R^1$=4-(N-piperidino)-, $R^8$=$CH_3$, $R^{12}$=H) and another 1.04 g of slightly impure material in overall 78% yield. $^1$H NMR (250 MHz $CDCl_3$) δ 6.96 (d, 2, J=8.5 Hz, ArH), 6.80 (d, 2, J=8.6 Hz, ArH), 5.77 (s, 1, $C_4$ H), 4.32 (d, 1, J=6.1 Hz, $C_{11α}$ H), 3.08 (br t, 4, N($CH_2$)$_2$), 2.09 (s, 3, ON═C—$CH_3$), 0.68 (s, 3, $C_{18}$ $CH_3$); mass spectrum, m/z (rel intensity) 498 (49), 481 (54), 320 (22), 174 (100), 161 (40), Anal. Calcd for $C_{30}H_{38}N_2O_2$•1.75 $H_2O$: C, 74.75; H, 8.65; N, 5.28. Found: C, 74.76; H, 8.56; N, 5.26.

The biological activity of the compounds of this invention was examined by means of in vitro and in vivo tests.

Receptor Binding:

The affinity of the compounds for hormone receptors for progestins and glucocorticoids from rabbits was determined by standard procedures similar to those that have been described in C. E. Cook, et al., *Human Reproduction*, Volume 9, supplement 1, pp. 32–39 (1994). However, the source of the glucocorticoid receptor was the thymus of the estrogen-primed immature female rabbit. The affinity of the compounds for the human progesterone hormone receptor was determined by standard procedures similar to those that have been described in Horwitz, et al., *Cell*, 28: 633–42 (1982) and Mockus, et al., *Endocrinology*, 110: 1564–71 (1982). The receptor was obtained in cytosol from human T-47D breast cells and [$^3$H]-R5020 was used as the radioligand. T47D cells (1 billion/mL) were homogenized in TEDG buffer (10 mM Tris, 1.5 mM EDTA, 1 mM dithiothreitol, 1 mM sodium molybdate, and 10% glycerol) using a Dounce pestle A, and the homogenate was centrifuged at 34,000×g for 1 hour. The supernatant was stored at −80° C. An aliquot of receptor preparation was combined with test compound, 0.4 nM [$^3$H]-R5020, and TEDG buffer to a final volume of 150 μL and incubated for 4 hours at 4° C. in microtiter plates. At the end of incubation 40 μL 40% polyethylene glycol and 15 μL 1% human gamma globulin was added to the incubate and the contents of each well were harvested onto double thick B filter mats (Wallac LKB) using a TomTec harvester. A film of Meltilux scintillant wax was applied to the dried filter mats and the mats were counted in a scintillation counter to determine inhibition of [$^3$H]-R5020 binding. Data are expressed as IC$_{50}$ values, i.e., the concentration of compound that inhibits radioligand binding by 50%.

Table 1 shows that compounds of the present invention bind strongly to the progestin receptor but with varying degrees of affinity. Of particular note is the surprising high ratio of affinity for the progestin receptor as compared with the glucocorticoid receptor. Such compounds are advantageous in diminishing or eliminating the antiglucorticoid effects associated with known antiprogestins such as mifepristone. Table 2 shows that the high affinity for the rabbit progestin receptor extends to the human receptor as well.

Cellular and animal tests were also performed to further characterize the biological activity of the compounds of the invention.

Determination of Progestational and Antiprogestational Activity in Human Cells:

Human T-47D breast cells grown in nutrient media were incubated with the standard progestin R5020 alone or with R5020 plus test compound and then assessed by standard procedures for proliferation using incorporation of [$^3$H]-thymidine as the measurement. Table 3 shows results of these assays. Data for antiprogestin activity are expressed as EC$_{50}$, i.e., the concentration of compound which inhibits 0.15 nM R5020-mediated proliferation by 50%. The maximum % inhibition (a measure of the efficacy of the compounds) is also given. In the agonist format of this assay the compounds were tested at concentrations ranging from 0.01 to 10 nM and the maximum % stimulation at any dose is listed in Table 3. It can be seen that in this assay some of the compounds exhibit potent antiprogestational activity, but that there is also some agonist activity associated with them as well.

Determination of Progestational and Antiprogestational Activity In Vivo:

Progestational activity and antiprogestational activity were determined in rabbits by means of the McGinty test (test compound alone, procedure of McGinty et al., *Endocrinology*, 24: 829–832 (1939)) or anti-McGinty test (test compound plus progesterone, procedure of Tamara et al., *Jpn. J. Fertil Steril* 24: 48–81 (1979)). Results were scored according to McPhail (McPhail, *J Physiol.*, 83: 146 (1934)). These are standard procedures known to those skilled in the art. The results of these assays are shown in Tables 4 (agonist activity) and 5 (antagonist activity). It can be seen that one of the nitrone compounds (II, R$^1$=4-Me$_2$N—, X=0, R$^6$=R$^{12}$=H, R$^8$=CH$_3$), which exhibited an excellent separation of progestin and glucocorticoid receptor affinity, was a potent antiprogestin in the anti-McGinty assay. Other compounds, such as I (R$^1$=4-CH$_3$CO—, X=0, R$^6$=R$^{12}$=H, R$^7$=CC—CH$_3$), exhibited a mixed (agonist/antagonist) profile. Compound I (R$^1$=4-Me$_2$N—, X=0, R$^6$=R$^{12}$=H, R$^7$=CC—CH$_3$) was a potent antiprogestin when given orally to estrogen-primed immature female rabbits together with subcutaneous progesterone in the anti-Clauberg assay and scored by the McPhail Index ((McPhail, *J. Physiol.*, 83: 146 (1934)).

The 11β-aryl-17β-nitro compounds of the present invention bind with good affinity to the progestin receptor (Tables 1 and 2) and have antiprogestational activity in vitro (Table 3) or in vivo Table 5). The 17,17-spironitrone compounds of the invention not only bind strongly to the progestin receptor (Table 1) and demonstrate antiprogestational activity (Table 5), but also bind weakly to the glucocorticoid receptor (Table 1), thus markedly diminishing the likelihood of their having significant glucocorticoid or antiglucocorticoid activity. The latter is a significant side-effect with current antiprogestins such as mifepristone.

TABLE 1

| | | | | | | | Receptor Binding (Rabbit) | | |
| | | | | | | | Relative Binding Affinity[a] | | |
| Structure | R$^1$ | R$^{12}$ | X | R$^6$ | R$^7$ | R$^8$ | rPR Relative Affinity (Progesterone) | rGR Relative Affinity (Dexamethasone) | Ratio PR/GR |
| --- | --- | --- | --- | --- | --- | --- | --- | --- | --- |
| II | 4-Me$_2$N | H | O | H | — | CH$_3$ | 157 | 2 | 78.5 |
| II | 4-CH$_3$CO | H | O | H | — | CH$_3$ | 21 | — | — |
| I | 4-Me$_2$N | H | O | H | —CC—CH$_3$ | — | 55 | 36 | 1.5 |
| I | 4-Me$_2$N | H | O | H | CH=CHCH$_2$OH | — | 56 | 16 | 3.5 |
| I | 4-Me$_2$N | H | O | H | —(CH$_2$)$_3$OH | — | 170 | 74 | 2.3 |
| I | 4-CH$_3$CO | H | O | H | —CC—CH$_3$ | — | 153 | 20 | 7.7 |
| I | 4-CH$_3$CO | H | O | H | CH=CHCH$_2$OH | — | 26 | 4 | 6.5 |
| I | 4-CH$_3$CO | H | O | H | —(CH$_2$)$_3$OH | — | 53 | 3 | 17.7 |
| I | 4-MeS | H | O | H | CH=CHCH$_2$OH | — | 32 | — | — |

TABLE 1-continued

Receptor Binding (Rabbit)

| | | | | | | | Relative Binding Affinity[a] | | |
|---|---|---|---|---|---|---|---|---|---|
| Structure | R[1] | R[12] | X | R[6] | R[7] | R[8] | rPR Relative Affinity (Progesterone) | rGR Relative Affinity (Dexamethasone) | Ratio PR/GR |
| I | 4-MeS | H | O | H | —(CH$_2$)$_3$OH | — | 61 | 3 | 20.3 |
| I | 4-MeS(O) | H | O | H | —(CH$_2$)$_3$OH | — | 23 | <2 | >10 |

[a]Values are determined relative to progesterone = 100 (for progestin receptor) or dexamethasone = 100 (for glucocorticocoid receptor)

TABLE 2

Receptor Binding (Human)

| Structure | R[1] | R[12] | X | R[6] | R[7] | R[8] | Relative Binding Affinity hPR IC$_{50}$ (nM) |
|---|---|---|---|---|---|---|---|
| II | 4-Me$_2$N | H | O | H | — | CH$_3$ | 10.2 |
| II | 4-Me$_2$N | H | O | H | — | H | 18 |
| I | 4-Me$_2$N | H | O | H | —(CH$_2$)$_3$OH | — | 4.1 |
| I | 4-CH$_3$CO | H | O | H | —CC—CH$_3$ | — | 0.8 |
| I | 4-CH$_3$CO | H | O | H | CH=CHCH$_2$OH | — | 26.1 |
| I | 4-CH$_3$CO | H | O | H | —(CH$_2$)$_3$OH | — | 16 |

TABLE 3

T47D Cell Activity

| | | | | | | | Cell Proliferation | | |
|---|---|---|---|---|---|---|---|---|---|
| | | | | | | | Antagonist Format | | Agonist |
| Structure | R[1] | R[12] | X | R[6] | R[7] | R[8] | EC$_{50}$ (nM) | % inhibition | % Stimulation |
| I | 4-Me$_2$N | H | O | H | —(CH$_2$)$_3$OH | — | 12 | 89 | 33 |
| I | 4-CH$_3$CO | H | O | H | —CC—CH$_3$ | — | 3.3 | 90 | 35 |
| I | 4-CH$_3$CO | H | O | H | —CH=CHCH$_2$OH | — | 122 | 86 | 52 |
| I | 4-CH$_3$CO | H | O | H | —(CH$_2$)$_3$OH | — | 175 | 96 | 41 |

TABLE 4

Progestational Activity

McGinty Assay (Agonist)

| | | | | | | | Dose (micrograms) | | |
|---|---|---|---|---|---|---|---|---|---|
| | | | | | | | 0.3 | 3 | 30 |
| Structure | R[1] | R[12] | X | R[6] | R[7] | R[8] | McPhail Index | | |
| Vehicle | | | | | | | 0 | | |
| Standard (Progesterone) | | | | | | | 2.45 ± 0.14 | | |
| II | 4-Me$_2$N | H | O | H | — | CH$_3$ | 0 ± 0 | 0 ± 0 | 0 ± 0 |
| II | 4-Me$_2$N | H | O | H | — | H | 0 ± 0 | 0 ± 0 | 0 ± 0 |
| I | 4-Me$_2$N | H | O | H | —(CH$_2$)$_3$OH | — | 0 ± 0 | 0 ± 0 | 0.03 ± 0.057 |
| I | 4-CH$_3$CO | H | O | H | —CC—CH$_3$ | — | 0.13 ± 0.12 | 1.33 ± 0.35 | 0.97 ± 0.75 |
| I | 4-CH$_3$CO | H | O | H | —CH=CHCH$_2$OH | — | 0 ± 0 | 0 ± 0 | 0 ± 0 |
| I | 4-CH$_3$CO | H | O | H | —(CH$_2$)$_3$OH | — | 0 ± 0 | 0 ± 0 | 0 ± 0 |

TABLE 5

Antiprogestational Activity

Anti-McGinty Assay (Antagonist)

| | | | | | | Dose (micrograms) | | |
|---|---|---|---|---|---|---|---|---|
| | | | | | | 0.3 | 3 | 30 |
| Structure | $R^1$ | $R^{12}$ | X | $R^6$ | $R^7$ | $R^8$ | McPhail Index | |
| Vehicle | | | | | | | 0 | |
| Standard (Progesterone) | | | | | | | 2.45 ± 0.14 | |
| II | 4-Me$_2$N | H | O | H | — | CH$_3$ | 2.03 ± 0.14 | 1.9 ± 0.85 | 0 ± 0 |
| II | 4-Me$_2$N | H | O | H | — | H | 2.0 ± 0.11 | 1.83 ± 0.2 | 0.23 ± 0.23 |
| I | 4-Me$_2$N | H | O | H | —(CH$_2$)$_3$OH | — | 1.83 ± 0.48 | 1.87 ± 0.98 | 0.43 ± 0.31 |
| I | 4-CH$_3$CO | H | O | H | —CC—CH$_3$ | — | 2.173 ± 0.42 | 2.47 ± 0.15 | 0.13 ± 0.12 |
| I | 4-CH$_3$CO | H | O | H | —CH=CHCH$_2$OH | — | 1.53 ± 0.68 | 1.76 ± 0.45 | 2.3 ± 0.0 |
| I | 4-CH$_3$CO | H | O | H | —(CH$_2$)$_3$OH | — | 2.93 ± 0.12 | 2.43 ± 0.6 | 1.60 ± 0.66 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A hormonal or antihormonal steroid compound of structure I,

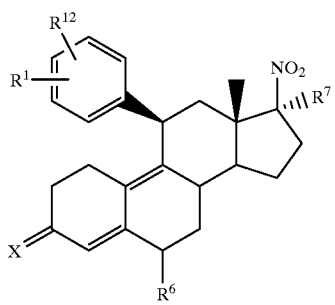

(I)

wherein $R^1$ is $(R^2R^3N(O)_r)$—, where r is 0 or 1 and $R^2$ and $R^3$ are each independently H, $C_{1-6}$ alkyl, $C_{3-8}$ cycloalkyl, $C_{2-6}$ alkenyl or $C_{2-6}$ alkynyl, any of which may be optionally substituted; or $R^1$ is halo-, HO—, $CF_3SO_2O$—, $C_{1-6}$ alkyl O—, $C_{1-6}$ alkyl S—, $C_{1-6}$ alkyl S(O)—, $C_{1-6}$ alkyl S(O$_2$)—, $C_{1-6}$ alkyl CO—, $C_{1-6}$ alkyl CH(OH)—, NC—, HC≡C—, $C_6H_5C$≡C—, $C_6H_5$—, $H_2C$≡CH—, $C_{1-6}$ alkyl or MeC(=CH$_2$)-; and $R^{12}$ is H or halo; or X is O or NOR$^5$, where R$^5$ is H or $C_{1-6}$ alkyl, $C_{3-8}$ cycloalkyl, $C_{2-6}$ alkenyl, $C_{2-6}$ alkynyl or $C_{6-12}$ aryl, any of which may be optionally substituted; or X is (H, H), (H, OH), (H, OSi($C_{1-6}$ alkyl)$_3$), or (H, OCOR$^5$), where R$^5$ is $C_{1-6}$ alkyl, $C_{3-8}$ cycloalkyl, $C_{2-6}$ alkenyl, $C_{2-6}$ alkynyl, $C_{6-12}$ aryl, aralkyl, aralkenyl or aralkynyl, any of which may be optionally substituted; or $R^6$ is H, $C_{1-6}$ alkyl, or halogen;

$R^7$ is H, $C_{1-6}$ alkyl, $C_{2-6}$ alkenyl, or $C_{2-6}$ alkynyl, $C_{3-8}$ cycloalkyl, $C_{6-12}$ aryl, aralkyl, aralkenyl or aralkynyl, any of which may be optionally substituted, and pharmaceutically acceptable salts thereof.

2. The steroid having structure I of claim 1, wherein $R^1$-Ph is 4-aminophenyl, 4-(N-methylamino)phenyl or 4-(N,N-dimethylamino)phenyl;

X is O, NOH, or NOCH$_3$;

$R^6$ is H, CH$_3$, F or Cl;

$R^7$ is H, methyl, ethynyl, 1-propynyl, 3-propynyl, 3-hydroxypropyl, 3-hydroxy-1-propenyl (E- or Z-), 3,3,3-trifluropropyn-1-yl, 3-hydroxypropyn-1-yl, (CH$_2$)$_2$COOCH$_3$, (CH$_2$)$_2$COOC$_2$H$_5$, (CH$_2$)$_2$COCH$_3$, C≡C-$_6$H$_5$, or CH$_2$C$_6$H$_5$.

3. The steroid of claim 1, selected from the group consisting of: 11β-(4-acetylphenyl)-17α-(1-propynyl)-17β-nitroestra-4,9-dien-3-one; 11β-(4-(N,N-dimethylamino)phenyl)-17α-(1-propynyl)-17β-nitroestra-4,9-dien-3-one; 11β-(4-acetylphenyl)-17α-(E-3-hydroxy-1-propenyl)-17β-nitroestra-4,9-dien-3-one; 11β-(4-acetylphenyl)-17α-(3-hydroxypropyl)-17β-nitroestra-4,9-dien-3-one; 11β-(4-(N,N-dimethylamino)phenyl)-17α-(E-3-hydroxy-1-propenyl)-17β-nitroestra-4,9-dien-3-one and 11β-(4-(N,N-dimethylamino)phenyl)-17α-(3-hydroxypropyl)-17β-nitroestra-4,9-dien-3-one.

4. A method of therapeutically treating the activity of progesterone comprising administering a therapeutically effective amount of the compound of claim 1, to a patient in need thereof for a therapeutic purpose.

5. The method of claim 4, wherein said therapeutic purpose is the treatment of endometriosis or uterine fibroids.

6. The method of claim 4, wherein said therapeutic purpose is cervical ripening preparatory to labor and delivery of offspring.

7. The method of claim 4, wherein said therapeutic purpose is the control or regulation of fertility.

8. The method of claim 4, wherein said therapeutic purpose is hormone replacement therapy.

9. The method of claim 7, further comprising co-administration of a compound selected from the group consisting of a prostaglandin, an oxytocic, an estrogen and a mixture thereof.

* * * * *